US006054295A

United States Patent [19]
Chen

[11] Patent Number: 6,054,295
[45] Date of Patent: Apr. 25, 2000

[54] DNA MOLECULES ENCODING HUMAN NUCLEAR RECEPTOR PROTEINS

[75] Inventor: Fang Chen, North Wales, Pa.

[73] Assignee: Merck & Co., Inc., Rahway, N.J.

[21] Appl. No.: 09/141,000

[22] Filed: Aug. 26, 1998

Related U.S. Application Data

[60] Provisional application No. 60/078,633, Mar. 19, 1998, provisional application No. 60/062,922, Oct. 21, 1997, and provisional application No. 60/057,090, Aug. 27, 1997.

[51] Int. Cl.[7] .......................... C12N 15/12; C12N 15/63; C12N 5/10
[52] U.S. Cl. .................... 435/69.1; 435/320.1; 435/325; 536/23.5
[58] Field of Search .................................. 435/69.1, 325, 435/320.1; 536/23.5

[56] References Cited

FOREIGN PATENT DOCUMENTS

WO 88/03168  5/1988  WIPO .

OTHER PUBLICATIONS

Luo et al. (1997) Nature 388 : 778–782.
Sladek et al. (1997) Genomics 45 : 320–326.
National Center for Biotechnology Information, dbEST:394331, GenBankAcc. #H91890 Retrieved from National Library of Medicine,National Center for Bio. Info, Bethesda, MD, Nov. 29, 1995.
National Center for Biotechnology Inforamtion, dbEST:533950, GenBank Acc. #W26275 Retrieved from National Library of Medicine,National Center for Bio. Info, Bethesda, MD, May 8, 1996.
Giguere et al. 'Identification of a new class of steroid hormone receptors'; Nature, vol. 331, Jan. 7, 1988, pp91–94.

Trapp et al. 'Nuclear Orphan Receptor as a Repressor of Glucocorticoid Receptor Transcriptional Activity'; The Journal of Biological Chemistry, vol. 271, No. 17, issue of Apr. 26, pp 9879–9882, 1996.

Tsai et al. 'Molecular Mechanisms of Action of Steroid/Thyroid Receptor Superfamily Members', Annu. Rev. Biochem. 1994, 63: 451–86.

Tontonoz et al. 'Stimulatio of Adipogenesis of Fibroblasts by PPAR 2, a Lipid–Activated Transcription Factor', Cell vol. 79, 1147–1156, Dec. 30, 1994.

Lehmann et al. An Antidiabetic Thia zolidinedione is a High Affinity Ligand for Peroxisome Proliferator–activated Receptor (PPAR ); The Jour. of Biol. Chem. vol. 270, No. 22, Issue of Jun. 2, pp 12953–12956, 1995.

Teboul et al. 'Thiazolidinediones and Fatty Acids Convert Myogenic Cells in Adipose like Cells', The Jour. of Biol. Chem. vol. 270, No. 47, issue of Nov. 24, 1995 pp 28183–28187.

Pettersson et al 'Expression of a novel member of estrogen response element–binding nuclear receptors is restricted to the early stages of chorion formation during mouse embryogenesis', Mechanisms of Development, vol. 54, No. 2 pp 211–223, 1996.

*Primary Examiner*—Paula K. Hutzell
*Assistant Examiner*—Michael Pak
*Attorney, Agent, or Firm*—J. Mark Hand; Jack L. Tribble

[57] ABSTRACT

The present invention discloses the isolation and characterization of cDNA molecules encoding two human nuclear receptor proteins, designated nNR1, nNR2 and/or nNR2-1. Also within the scope of the disclosure are recombinant vectors, recombinant host cells, methods of screening for modulators of nNR1, nNR2 and/or nNR2-1 activity, and production of antibodies against nNR1, nNR2 and/or nNR2-1, or epitopes thereof.

22 Claims, 26 Drawing Sheets

1    GAATATGATG ACCCTAATGC AACAATATCT AACATACTAT CCGAGCTTCG

51   GTCATTTGGA AGAACTGCAG ATTTTCCTCC TTCAAAATTA AAGTCAGGTT

101  ATGGAGAACA TGTATGCTAT GTTCTTGATT GCTTCGCTGA AGAAGCATTG

151  AAATATATTG GTTTCACCTG GAAAAGGCCA ATATACCCAG TAGAAGAATT

201  AGAAGAAGAA AGCGTTGCAG AAGATGATGC AGAATTAACA TTAAATAAAG

251  TGGATGAAGA ATTTGTGGAA GAAGAGACAG ATAATGAAGA AAACTTTATT

301  GATCTCAACG TTTTAAAGGC CCAGACATAT CACTTGGATA TGAACGAGAC

351  TGCCAAACAA GAAGATATTT TGGAATCCAC AACAGATGCT GCAGAATGGA

401  GCCTAGAAGT GGAACGTGTA CTACCGCAAC TGAAAGTCAC GATTAGGACT

451  GACAATAAGG ATTGGAGAAT CCATGTTGAC CAAATGCACC AGCACAGAAG

501  TGGAATTGAA TCTGCTCTAA AGGAGACCAA GGGATTTTTG GACAAACTCC

551  ATAATGAAAT TACTAGGACT TTGGAAAAGA TCAGCAGCCG AGAAAAGTAC

601  ATCAACAATC AGCCGGGAGC CCATGGAGCA CTGTCCTCAG AGATGCGCAG

651  GTTAGGCTCA CTGTCTAGGC CAGGCCCACC TTAGTCACTG TGGACTGGCA

701  ATGGAAGCTC TTCCTGGACA CACCTGCCCT AGCCCTCACC CTGGGGTGGA

751  AGAGAAATGA GCTTGGCTTG CAACTCAGAC CATTCCACGG AGGCATCCTC

801  CCCTTCCCTG GGCTGGTGAA TAAAAGTTTC CTGAGGTCAA GGACTTCCTT

851  TTCCCTGCCA AAATGGTGTC CAGAACTTTG AGGCCAGAGG TGATCCAGTG

FIG.1A

```
 901   ATTTGGGAGC TGCAGGTCAC ACAGGCTGCT CAGAGGGCTG CTGAACAGGA

951   TGTCCTCGGA CGACAGGCAC CTGGGCTCCA GCTGCGGCTC CTTCATCAAG

1001   ACTGAGCCGT CCAGCCCGTC CTCGGGCATA GATGCCCTCA GCCACCACAG

1051   CCCCAGTGGC TCGTCCGACG CCAGCGGCGG CTTTGGCCTG GCCCTGGGCA

1101   CCCACGCCAA CGGTCTGGAC TCGCCACCCA TGTTTGCAGG CGCCGGGCTG

1151   GGAGGCACCC CATGCCGCAA GAGCTACGAG GACTGTGCCA GCGGCATCAT

1201   GGAGGACTCG GCCATCAAGT GCGAGTACAT GCTCAACGCC ATCCCCAAGC

1251   GCCTGTGCCT CGTGTGCGGG GACATTGCCT CTGGCTACCA CTACGGCGTG

1301   GCCTCCTGCG AGGCTTGCAA GGCCTTCTTC AAGAGGACTA TCCAAGGGAA

1351   CATTGAGTAC AGCTGCCCGG CCACCAACGA GTGCGAGATC ACCAAACGGA

1401   GGCGCAAGTC CTGCCAGGCC TGCCGCTTCA TGAAATGCCT CAAAGTGGGG

1451   ATGCTGAAGG AAGGTGTGCG CCTTGATCGA GTGCGTGGAG GCCGTCAGAA

1501   ATACAAGCGA CGGCTGGACT CAGAGAGCAG CCCATACCTG AGCTTACAAA

1551   TTTCTCCACC TGCTAAAAAG CCATTGACCA AGATTGTCTC ATACCTACTG

1601   GTGGCTGAGC CGGACAAGCT CTATGCCATG CCTCCCCCTG GTATGCCTGA

1651   GGGGGACATC AAGGCCCTGA CCACTCTCTG TGACCTGGCA GACCGAGAGC

1701   TTGTGGTCAT CATTGGCTGG GCCAAGCACA TCCCAGGCTT CTCAAGCCTC

1751   TCCCTGGGGG ACCAGATGAG CCTGCTGCAG AGTGCCTGGA TGGAAATCCT
```

FIG.1B

```
1801  CATCCTGGGC ATCGTGTACC GCTCGCTGCC CTACGACGAC AAGCTGGTGT

1851  ACGCTGAGGA CTACATCATG GATGAGGAGC ACTCCCGCCT CGCGGGGCTG

1901  CTGGAGCTCT ACCGGGCCAT CCTGCAGCTG GTACGCAGGT ACAAGAAGCT

1951  CAAGGTGGAG AAGGAGGAGT TTGTGACGCT CAAGGCCCTG GCCCTCGCCA

2001  ACTCCGATTC CATGTACATC GAGGATCTAG AGGCTGTCCA GAAGCTGCAG

2051  GACCTGCTGC ACGAGGCACT GCAGGACTAC GAGCTGAGCC AGCGCCATGA

2101  GGAGCCCTGG AGGACGGGCA AGCTGCTGCT GACACTGCCG CTGCTGCGGC

2151  AGACGGCCGC CAAGGCCGTG CAGCACTTCT ATAGCGTCAA ACTGCAGGGC

2201  AAAGTGCCCA TGCACAAACT CTTCCTGGAG ATGCTGGAGG CCAAGGCCTG

2251  GGCCAGGGCT GACTCCCTTC AGGAGTGGAG GCCACTGGAG CAAGTGCCCT

2301  CTCCCCTCCA CCGAGCCACC AAGAGGCAGC ATGTGCATTT CCTAACTCCC

2351  TTGCCCCCTC CCCCATCTGT GGCCTGGGTG GGCACTGCTC AGGCTGGATA

2401  CCACCTGGAG GTTTTCCTTC CGCAGAGGGC AGGTTGGCCA AGAGCAGCTT

2451  AGAGGATCTC CCAAGGATGA AAGAATGTCA AGCCATGATG GAAAATGCCC

2501  CTTCCAATCA GCTGCCTTCA CAAGCAGGGA TCAGAGCAAC TCCCCGGGGA

2551  TCCCCAATCC ACGCCCTTCT AGTCCAACCC CCTCAATGA GAGAGGCAGG

2601  CAGATCTCAC CCAGCACTAG GACACCAGGA GGCCAGGGAA AGCATCTCTG

2651  GCTCACCATG TAACATCTGG CTTGGAGCAA GTGGGTGTTC TGCACACCAG

2701  GCAGCTGCAC CTCACTGGAT CTAGTGTTGC TGCGAGTGAC CTCACTTCAG

2751  AGCCCCTCTA GCAGAGTGGG GCGGAAGTCC TGATGGTTGG TGTCCATGAG

2801  GTGGAAG (SEQ.ID NO:1)
```

FIG. 1C

```
            GAATATGATGACCCTAATGCAACAATATCTAACATACTATCCGAGCTTCGGTCATTTGGA
        1   ----------+----------+----------+----------+----------+----------+ 60
            CTTATACTACTGGGATTACGTTGTTATAGATTGTATGATAGGCTCGAAGCCAGTAAACCT

AGAACTGCAGATTTTCCTCCTTCAAAATTAAAGTCAGGTTATGGAGAACATGTATGCTAT
       61   ----------+----------+----------+----------+----------+----------+ 120
            TCTTGACGTCTAAAAGGAGGAAGTTTTAATTTCAGTCCAATACCTCTTGTACATACGATA

GTTCTTGATTGCTTCGCTGAAGAAGCATTGAAATATATTGGTTTCACCTGGAAAAGGCCA
      121   ----------+----------+----------+----------+----------+----------+ 180
            CAAGAACTAACGAAGCGACTTCTTCGTAACTTTATATAACCAAAGTGGACCTTTTCCGGT

ATATACCCAGTAGAAGAATTAGAAGAAGAAAGCGTTGCAGAAGATGATGCAGAATTAACA
      181   ----------+----------+----------+----------+----------+----------+ 240
            TATATGGGTCATCTTCTTAATCTTCTTCTTTCGCAACGTCTTCTACTACGTCTTAATTGT

TTAAATAAAGTGGATGAAGAATTTGTGGAAGAAGAGACAGATAATGAAGAAAACTTTATT
      241   ----------+----------+----------+----------+----------+----------+ 300
            AATTTATTTCACCTACTTCTTAAACACCTTCTTCTCTGTCTATTACTTCTTTTGAAATAA

GATCTCAACGTTTTAAAGGCCCAGACATATCACTTGGATATGAACGAGACTGCCAAACAA
      301   ----------+----------+----------+----------+----------+----------+ 360
            CTAGAGTTGCAAAATTTCCGGGTCTGTATAGTGAACCTATACTTGCTCTGACGGTTTGTT

GAAGATATTTTGGAATCCACAACAGATGCTGCAGAATGGAGCCTAGAAGTGGAACGTGTA
      361   ----------+----------+----------+----------+----------+----------+ 420
            CTTCTATAAAACCTTAGGTGTTGTCTACGACGTCTTACCTCGGATCTTCACCTTGCACAT

CTACCGCAACTGAAAGTCACGATTAGGACTGACAATAAGGATTGGAGAATCCATGTTGAC
      421   ----------+----------+----------+----------+----------+----------+ 480
            GATGGCGTTGACTTTCAGTGCTAATCCTGACTGTTATTCCTAACCTCTTAGGTACAACTG

CAAATGCACCAGCACAGAAGTGGAATTGAATCTGCTCTAAAGGAGACCAAGGGATTTTTG
      481   ----------+----------+----------+----------+----------+----------+ 540
            GTTTACGTGGTCGTGTCTTCACCTTAACTTAGACGAGATTTCCTCTGGTTCCCTAAAAAC
```

FIG.2A

```
     GACAAACTCCATAATGAAATTACTAGGACTTTGGAAAAGATCAGCAGCCGAGAAAAGTAC
541  ---------+---------+---------+---------+---------+---------+  600
     CTGTTTGAGGTATTACTTTAATGATCCTGAAACCTTTTCTAGTCGTCGGCTCTTTTCATG

ATCAACAATCAGCCGGGAGCCCATGGAGCACTGTCCTCAGAGATGCGCAGGTTAGGCTCA
601  ---------+---------+---------+---------+---------+---------+  660
     TAGTTGTTAGTCGGCCCTCGGGTACCTCGTGACAGGAGTCTCTACGCGTCCAATCCGAGT

CTGTCTAGGCCAGGCCCACCTTAGTCACTGTGGACTGGCAATGGAAGCTCTTCCTGGACA
661  ---------+---------+---------+---------+---------+---------+  720
     GACAGATCCGGTCCGGGTGGAATCAGTGACACCTGACCGTTACCTTCGAGAAGGACCTGT

CACCTGCCCTAGCCCTCACCCTGGGGTGGAAGAGAAATGAGCTTGGCTTGCAACTCAGAC
721  ---------+---------+---------+---------+---------+---------+  780
     GTGGACGGGATCGGGAGTGGGACCCCACCTTCTCTTTACTCGAACCGAACGTTGAGTCTG

CATTCCACGGAGGCATCCTCCCCTTCCCTGGGCTGGTGAATAAAAGTTTCCTGAGGTCAA
781  ---------+---------+---------+---------+---------+---------+  840
     GTAAGGTGCCTCCGTAGGAGGGGAAGGGACCCGACCACTTATTTTCAAAGGACTCCAGTT

GGACTTCCTTTTCCCTGCCAAAATGGTGTCCAGAACTTTGAGGCCAGAGGTGATCCAGTG
841  ---------+---------+---------+---------+---------+---------+  900
     CCTGAAGGAAAAGGGACGGTTTTACCACAGGTCTTGAAACTCCGGTCTCCACTAGGTCAC

ATTTGGGAGCTGCAGGTCACACAGGCTGCTCAGAGGGCTGCTGAACAGGATGTCCTCGGA
901  ---------+---------+---------+---------+---------+---------+  960
     TAAACCCTCGACGTCCAGTGTGTCCGACGAGTCTCCCGACGACTTGTCCTACAGGAGCCT
                                                        M  S  S  D

CGACAGGCACCTGGGCTCCAGCTGCGGCTCCTTCATCAAGACTGAGCCGTCCAGCCCGTC
961  ---------+---------+---------+---------+---------+---------+  1020
     GCTGTCCGTGGACCCGAGGTCGACGCCGAGGAAGTAGTTCTGACTCGGCAGGTCGGGCAG
      D  R  H  L  G  S  S  C  G  S  F  I  K  T  E  P  S  S  P  S
```

FIG.2B

```
       CTCGGGCATAGATGCCCTCAGCCACCACAGCCCCAGTGGCTCGTCCGACGCCAGCGGCGG
1021   ---------+---------+---------+---------+---------+---------+ 1080
       GAGCCCGTATCTACGGGAGTCGGTGGTGTCGGGGTCACCGAGCAGGCTGCGGTCGCCGCC
        S  G  I  D  A  L  S  H  H  S  P  S  G  S  S  D  A  S  G  G

CTTTGGCCTGGCCCTGGGCACCCACGCCAACGGTCTGGACTCGCCACCCATGTTTGCAGG
1081   ---------+---------+---------+---------+---------+---------+ 1140
       GAAACCGGACCGGGACCCGTGGGTGCGGTTGCCAGACCTGAGCGGTGGGTACAAACGTCC
        F  G  L  A  L  G  T  H  A  N  G  L  D  S  P  P  M  F  A  G

CGCCGGGCTGGGAGGCACCCCATGCCGCAAGAGCTACGAGGACTGTGCCAGCGGCATCAT
1141   ---------+---------+---------+---------+---------+---------+ 1200
       GCGGCCCGACCCTCCGTGGGGTACGGCGTTCTCGATGCTCCTGACACGGTCGCCGTAGTA
        A  G  L  G  G  T  P  C  R  K  S  Y  E  D  C  A  S  G  I  M

GGAGGACTCGGCCATCAAGTGCGAGTACATGCTCAACGCCATCCCCAAGCGCCTGTGCCT
1201   ---------+---------+---------+---------+---------+---------+ 1260
       CCTCCTGAGCCGGTAGTTCACGCTCATGTACGAGTTGCGGTAGGGGTTCGCGGACACGGA
        E  D  S  A  I  K  C  E  Y  M  L  N  A  I  P  K  R  L  C  L
                                                                ‾  ‾

CGTGTGCGGGGACATTGCCTCTGGCTACCACTACGGCGTGGCCTCCTGCGAGGCTTGCAA
1261   ---------+---------+---------+---------+---------+---------+ 1320
       GCACACGCCCCTGTAACGGAGACCGATGGTGATGCCGCACCGGAGGACGCTCCGAACGTT
        V  C  G  D  I  A  S  G  Y  H  Y  G  V  A  S  C  E  A  C  K
        ‾  ‾  ‾  ‾  ‾  ‾  ‾  ‾  ‾  ‾  ‾  ‾  ‾  ‾  ‾  ‾  ‾  ‾  ‾  ‾

GGCCTTCTTCAAGAGGACTATCCAAGGGAACATTGAGTACAGCTGCCCGGCCACCAACGA
1321   ---------+---------+---------+---------+---------+---------+ 1380
       CCGGAAGAAGTTCTCCTGATAGGTTCCCTTGTAACTCATGTCGACGGGCCGGTGGTTGCT
        A  F  F  K  R  T  I  Q  G  N  I  E  Y  S  C  P  A  T  N  E
        ‾  ‾  ‾  ‾  ‾  ‾  ‾  ‾  ‾  ‾  ‾  ‾  ‾  ‾  ‾  ‾  ‾  ‾  ‾  ‾

GTGCGAGATCACCAAACGGAGGCGCAAGTCCTGCCAGGCCTGCCGCTTCATGAAATGCCT
1381   ---------+---------+---------+---------+---------+---------+ 1440
       CACGCTCTAGTGGTTTGCCTCCGCGTTCAGGACGGTCCGGACGGCGAAGTACTTTACGGA
        C  E  I  T  K  R  R  R  K  S  C  Q  A  C  R  F  M  K  C  L
        ‾  ‾  ‾  ‾  ‾  ‾  ‾  ‾  ‾  ‾  ‾  ‾  ‾  ‾  ‾  ‾  ‾  ‾  ‾  ‾
```

FIG.2C

```
     CAAAGTGGGGATGCTGAAGGAAGGTGTGCGCCTTGATCGAGTGCGTGGAGGCCGTCAGAA
1441 ---------+---------+---------+---------+---------+---------+ 1500
     GTTTCACCCCTACGACTTCCTTCCACACGCGGAACTAGCTCACGCACCTCCGGCAGTCTT
      K  V  G  M  L  K  E  G  V  R  L  D  R  V  R  G  G  R  Q  K

ATACAAGCGACGGCTGGACTCAGAGAGCAGCCCATACCTGAGCTTACAAATTTCTCCACC
1501 ---------+---------+---------+---------+---------+---------+ 1560
     TATGTTCGCTGCCGACCTGAGTCTCTCGTCGGGTATGGACTCGAATGTTTAAAGAGGTGG
      Y  K  R  R  L  D  S  E  S  S  P  Y  L  S  L  Q  I  S  P  P

TGCTAAAAAGCCATTGACCAAGATTGTCTCATACCTACTGGTGGCTGAGCCGGACAAGCT
1561 ---------+---------+---------+---------+---------+---------+ 1620
     ACGATTTTTCGGTAACTGGTTCTAACAGAGTATGGATGACCACCGACTCGGCCTGTTCGA
      A  K  K  P  L  T  K  I  V  S  Y  L  L  V  A  E  P  D  K  L

CTATGCCATGCCTCCCCCTGGTATGCCTGAGGGGGACATCAAGGCCCTGACCACTCTCTG
1621 ---------+---------+---------+---------+---------+---------+ 1680
     GATACGGTACGGAGGGGGACCATACGGACTCCCCCTGTAGTTCCGGGACTGGTGAGAGAC
      Y  A  M  P  P  P  G  M  P  E  G  D  I  K  A  L  T  T  L  C

TGACCTGGCAGACCGAGAGCTTGTGGTCATCATTGGCTGGGCCAAGCACATCCCAGGCTT
1681 ---------+---------+---------+---------+---------+---------+ 1740
     ACTGGACCGTCTGGCTCTCGAACACCAGTAGTAACCGACCCGGTTCGTGTAGGGTCCGAA
      D  L  A  D  R  E  L  V  V  I  I  G  W  A  K  H  I  P  G  F

CTCAAGCCTCTCCCTGGGGGACCAGATGAGCCTGCTGCAGAGTGCCTGGATGGAAATCCT
1741 ---------+---------+---------+---------+---------+---------+ 1800
     GAGTTCGGAGAGGGACCCCCTGGTCTACTCGGACGACGTCTCACGGACCTACCTTTAGGA
      S  S  L  S  L  G  D  Q  M  S  L  L  Q  S  A  W  M  E  I  L

CATCCTGGGCATCGTGTACCGCTCGCTGCCCTACGACGACAAGCTGGTGTACGCTGAGGA
1801 ---------+---------+---------+---------+---------+---------+ 1860
     GTAGGACCCGTAGCACATGGCGAGCGACGGGATGCTGCTGTTCGACCACATGCGACTCCT
      I  L  G  I  V  Y  R  S  L  P  Y  D  D  K  L  V  Y  A  E  D
```

FIG.2D

```
       CTACATCATGGATGAGGAGCACTCCCGCCTCGCGGGGCTGCTGGAGCTCTACCGGGCCAT
1861   ----------+---------+---------+---------+---------+---------+ 1920
       GATGTAGTACCTACTCCTCGTGAGGGCGGAGCGCCCCGACGACCTCGAGATGGCCCGGTA
        Y  I  M  D  E  E  H  S  R  L  A  G  L  L  E  L  Y  R  A  I

CCTGCAGCTGGTACGCAGGTACAAGAAGCTCAAGGTGGAGAAGGAGGAGTTTGTGACGCT
1921   ----------+---------+---------+---------+---------+---------+ 1980
       GGACGTCGACCATGCGTCCATGTTCTTCGAGTTCCACCTCTTCCTCCTCAAACACTGCGA
        L  Q  L  V  R  R  Y  K  K  L  K  V  E  K  E  E  F  V  T  L

CAAGGCCCTGGCCCTCGCCAACTCCGATTCCATGTACATCGAGGATCTAGAGGCTGTCCA
1981   ----------+---------+---------+---------+---------+---------+ 2040
       GTTCCGGGACCGGGAGCGGTTGAGGCTAAGGTACATGTAGCTCCTAGATCTCCGACAGGT
        K  A  L  A  L  A  N  S  D  S  M  Y  I  E  D  L  E  A  V  Q

GAAGCTGCAGGACCTGCTGCACGAGGCACTGCAGGACTACGAGCTGAGCCAGCGCCATGA
2041   ----------+---------+---------+---------+---------+---------+ 2100
       CTTCGACGTCCTGGACGACGTGCTCCGTGACGTCCTGATGCTCGACTCGGTCGCGGTACT
        K  L  Q  D  L  L  H  E  A  L  Q  D  Y  E  L  S  Q  R  H  E

GGAGCCCTGGAGGACGGGCAAGCTGCTGCTGACACTGCCGCTGCTGCGGCAGACGGCCGC
2101   ----------+---------+---------+---------+---------+---------+ 2160
       CCTCGGGACCTCCTGCCCGTTCGACGACGACTGTGACGGCGACGACGCCGTCTGCCGGCG
        E  P  W  R  T  G  K  L  L  L  T  L  P  L  L  R  Q  T  A  A

CAAGGCCGTGCAGCACTTCTATAGCGTCAAACTGCAGGGCAAAGTGCCCATGCACAAACT
2161   ----------+---------+---------+---------+---------+---------+ 2220
       GTTCCGGCACGTCGTGAAGATATCGCAGTTTGACGTCCCGTTTCACGGGTACGTGTTTGA
        K  A  V  Q  H  F  Y  S  V  K  L  Q  G  K  V  P  M  H  K  L

CTTCCTGGAGATGCTGGAGGCCAAGGCCTGGGCCAGGGCTGACTCCCTTCAGGAGTGGAG
2221   ----------+---------+---------+---------+---------+---------+ 2280
       GAAGGACCTCTACGACCTCCGGTTCCGGACCCGGTCCCGACTGAGGGAAGTCCTCACCTC
        F  L  E  M  L  E  A  K  A  W  A  R  A  D  S  L  Q  E  W  R
```

FIG.2E

```
      GCCACTGGAGCAAGTGCCCTCTCCCCTCCACCGAGCCACCAAGAGGCAGCATGTGCATTT
2281  ---------+---------+---------+---------+---------+---------+ 2340
      CGGTGACCTCGTTCACGGGAGAGGGGAGGTGGCTCGGTGGTTCTCCGTCGTACACGTAAA
       P  L  E  Q  V  P  S  P  L  H  R  A  T  K  R  Q  H  V  H  F

CCTAACTCCCTTGCCCCCTCCCCCATCTGTGGCCTGGGTGGGCACTGCTCAGGCTGGATA
2341  ---------+---------+---------+---------+---------+---------+ 2400
      GGATTGAGGGAACGGGGGAGGGGGTAGACACCGGACCCACCCGTGACGAGTCCGACCTAT
       L  T  P  L  P  P  P  P  S  V  A  W  V  G  T  A  Q  A  G  Y

CCACCTGGAGGTTTTCCTTCCGCAGAGGGCAGGTTGGCCAAGAGCAGCTTAGAGGATCTC
2401  ---------+---------+---------+---------+---------+---------+ 2460
      GGTGGACCTCCAAAAGGAAGGCGTCTCCCGTCCAACCGGTTCTCGTCGAATCTCCTAGAG
       H  L  E  V  F  L  P  Q  R  A  G  W  P  R  A  A  *  (SEQ ID NO:2)

CCAAGGATGAAAGAATGTCAAGCCATGATGGAAAATGCCCCTTCCAATCAGCTGCCTTCA
2461  ---------+---------+---------+---------+---------+---------+ 2520
      GGTTCCTACTTTCTTACAGTTCGGTACTACCTTTTACGGGGAAGGTTAGTCGACGGAAGT

CAAGCAGGGATCAGAGCAACTCCCCGGGGATCCCCAATCCACGCCCTTCTAGTCCAACCC
2521  ---------+---------+---------+---------+---------+---------+ 2580
      GTTCGTCCCTAGTCTCGTTGAGGGGCCCCTAGGGGTTAGGTGCGGGAAGATCAGGTTGGG

CCCTCAATGAGAGAGGCAGGCAGATCTCACCCAGCACTAGGACACCAGGAGGCCAGGGAA
2581  ---------+---------+---------+---------+---------+---------+ 2640
      GGGAGTTACTCTCTCCGTCCGTCTAGAGTGGGTCGTGATCCTGTGGTCCTCCGGTCCCTT

AGCATCTCTGGCTCACCATGTAACATCTGGCTTGGAGCAAGTGGGTGTTCTGCACACCAG
2641  ---------+---------+---------+---------+---------+---------+ 2700
      TCGTAGAGACCGAGTGGTACATTGTAGACCGAACCTCGTTCACCCACAAGACGTGTGGTC

GCAGCTGCACCTCACTGGATCTAGTGTTGCTGCGAGTGACCTCACTTCAGAGCCCCTCTA
2701  ---------+---------+---------+---------+---------+---------+ 2760
      CGTCGACGTGGAGTGACCTAGATCACAACGACGCTCACTGGAGTGAAGTCTCGGGGAGAT

GCAGAGTGGGGCGGAAGTCCTGATGGTTGGTGTCCATGAGGTGGAAG (SEQ ID NO:1)
2761  ---------+---------+---------+---------+------- 2807
      CGTCTCACCCCGCCTTCAGGACTACCAACCACAGGTACTCCACCTTC (SEQ ID NO:29)
```

FIG.2F

MSSDDRHLGS SCGSFIKTEP SSPSSGIDAL SHHSPSGSSD ASGGFGLALG

THANGLDSPP MFAGAGLGGT PCRKSYEDCA SGIMEDSAIK CEYMLNAIPK

RL<u>CLVCGDIA SGYHYGVASC EACKAFFKPT IQGNIEYSCP ATNICEITKR

RRKSCQACRF MKCLKVGM</u>LK EGVRLDRVRG GRQKYKRRLD SESSPYLSLQ

ISPPAKKPLT KIVSYLLVAE PDKLYAMPPP GMPRGDIKAL TTLCDLADRE

LVVIIGWAKH IPGFSSLSLG DQMSLLQSAW MEILILGIVY RSLPYDDKLV

YAEDYIMDEE HSRLAGLLEL YRAILQLVRR YKKLKVEKEE FVTLKALALA

NSDSMYIEDL EAVQKLQDLL HEALQDYELS QRHEEPWRTG KLLLTLPLLR

QTAAKAVQHF YSVKLQGKVP MHKLFLEMLE AKAWARADSL QEWRPLEQVP

SPLHRATKRQ HVHFLTPLPP PPSVAWVGTA QAGYHLEVFL PQRAGWPRAA (SEQ ID NO:2)

FIG.3

```
   1  GCGGGCCGCC AGTGTGGTGG AATTCGGCTT GTCACTAGGA ??????????
  51  GTTAATTGCA CTGTGCTCTG TCAAGGAAAC TTTGATTTAT AGCTGGGGTG
 101  CACAAATAAT GGTTGCCGGT CGCACATGGA TTCGGTAGAA CTTTGCCTTC
 151  CTGAATCTTT TTCCCTGCAC TACGAGGAAG AGCTTCTCTG CAGAATGTCA
 201  AACAAAGATC GACACATTGA TTCCAGCTGT TCGTCCTTCA TCAAGACGGA
 251  ACCTTCCAGC CCAGCCTCCC TGACGGACAG CGTCAACCAC CACAGCCCTG
 301  GTGGCTCTTC AGACGCCAGT GGGAGCTACA GTTCAACCAT GAATGGCCAT
 351  CAGAACGGAC TTGACTCGCC ACCTCTCTAC CCTTCTGCTC CTATCCTGGG
 401  AGGTAGTGGG CCTGTCAGGA AACTGTATGA TGACTGCTCC AGCACCATTG
 451  TTGAAGATCC CCAGACCAAG TGTGAATACA TGCTCAACTC GATGCCCAAG
 501  AGACTGTGTT TAGTGTGTGG TGACATCGCT TCTGGGTACC ACTATGGGGT
 551  AGCATCATGT GAAGCCTGCA AGGCATTCTT CAAGAGGACA ATTCAAGGCA
 601  ATATAGAATA CAGCTGCCCT GCCACGAATG AATGTGAAAT CACAAAGCGC
 651  AGACGTAAAT CCTGCCAGGC TTGCCGCTTC ATGAAGTGTT TAAAAGTGGG
 701  CATGCTGAAA GAAGGGGTGC GTCTTGACAG AGTACGTGGA GGTCGGCAGA
 751  AGTACAAGCG CAGGATAGAT GCGGAGAACA GCCCATACCT GAACCCTCAG
 801  CTGGTTCAGC CAGCCAAAAA GCCATATAAC AAGATTGTCT CACATTTGTT
 851  GGTGGCTGAA CCGGAGAAGA TCTATGCCAT GCCTGACCCT ACTGTCCCCG
 901  ACAGTGACAT CAAAGCCCTC ACTACAGTGT GTGACTTGGC CGACCGAGAG
 951  TTGGTGGTTA TCATTGGATG GGCGAAGCAT ATTCCAGGCT TCTCCACGCT
1001  GTCCCTGGCG GACCAGATGA GCCTTCTGCA GAGTGCTTGG ATGGAAATTT
1051  TGATCCTTGG TGTCGTATAC CGGTCTCTTT CATTTGAGGA TGAACTTGTC
```

FIG.4A

```
1101  TATGCAGACG ATTATATAAT GGACGAAGAC CAGTCCAAAT TAGCAGGCCT

1151  TCTTGATCTA AATAATGCTA TCCTGCAGCT GGTAAAGAAA TACAAGAGCA

1201  TGAAGCTGGA AAAAGAAGAA TTTGTCACCC TCAAAGCTAT AGCTCTTGCT

1251  AATTCAGACT CCATGCACAT AGAAGATGTT GAAGCCGTTC AGAAGCTTCA

1301  GGATGTCTTA CATGAAGCGC TGCAGGATTA TGAAGCTGGC CAGCACATGG

1351  AAGACCCTCG TCGAGCTGGC AAGATGCTGA TGACACTGCC ACTCCTGAGG

1401  CAGACCTCTA CCAAGGCCGT GCAGCATTTC TACAACATCA AACTAGAAGG

1451  CAAAGTCCCA ATGCACAAAC TTTTTTTGGA AATGTTGGAG CCAAGGTCT

1501  GACTAAAAGC TCCCTGGGCC TTCCCATCCT TCATGTTGAA AAAGGGAAAA

1551  TAAACCCAAG AGTGATGTCG AAGAAACTTA GAGTTTAGTT AACAACATCA

1601  AAAATCAACA GACTGCACTG ATAATTTAGC AGCAAGACTA TGAAGCAGCT

1651  TTCAGATTCC TCCATAGGTT CCTGATGAGT TCTTTCTACT TTCTCCATCA

1701  TCTTCTTTCC TCTTTCTTCC CACATTTCTC TTTCTCTTTA TTTTTTCTCC

1751  TTTTCTTCTT TCACCTCCCT TATTTCTTTG CTTCTTTCAT TCCTAGTTCC

1801  CATTCTCCTT TATTTTCTTC CCGTCTGCCT GCCTTCTTTC TTTTCTTTAC

1851  CTACTCTCAT TCCTCTCTTT TCTCATCCTT CCCCTTTTTT CTAAATTTGA

1901  AATAGCTTTA GTTTAAAAAA AAAAATCCTC CCTTCCCCCT TTCCTTTCCC

1951  TTTCTTTCCT TTTTCCCTTT CCTTTTCCCT TTCCTTTCCT TTCCTCTTGA

2001  CCTTCTTTCC ATCTTTCTTT TCTTCCTTC TGCTGCTGAA CTTTTAAAAG

2051  AGGTCTCTAA GTGAAGAGAG ATGGAAGCCA GCCCTGCCAA AGGATGGAGA

2101  TCCATAATAT GGATGCCAGT GAACTTATTG TGAACCATAC CGTCCCCAAT

2151  GACTAAGGAA TCAAAGAGAG AGAACCAACG TTCCTAAAAG TACAGTGCAA

2201  CATATACAAA TTGACTGAGT GCAGTATTAG ATTTCATGGG AGCAGCCTCT
```

FIG.4B

2251 AATTAGACAA CTTAAGCAAC GTTGCATCGG CTGCTTCTTA TCATTGCTTT

2301 TCCATCTAGA TCAGTTACAG CCATTTGATT CCTTAATTGT TTTTTCAAGT

2351 CTTCCAGGTA TTTGTTAGTT TAGCTACTAT GTAACTTTTT CAGGGAATAG

2401 TTTAAGCTTT ATTCATTCAT GCAATACTAA AGAGAAATAA GAATACTGCA

2451 ATTTTGTGCT GGCTTTGAAC AATTACGAAC AATAATGAAG GACAAATGAA

2501 TCCTGAAGGA AGATTTTTAA AAATGTTTTG TTTCTTCTTA CAAATGGAGA

2551 TTTTTTTGTA CCAGCTTTAC CACTTTTCAG CCATTTATTA ATATGGGAAT

2601 TTAACTTACT CAAGCAATAG TTGAAGGGAA GGTGCATATT ATCACGGATG

2651 CAATTTATGT TGTGTGCCAG TCTGGTCCCA AACATCAATT TCTTAACATG

2701 AGCTCCAGTT TACCTAAATG TTCACTGACA CAAAGGATGA GATTACACCT

2751 ACAGTGACTC TGAGTAGTCA CATATATAAG CACTGCACAT GAGATATAGA

2801 TCCGTAGAAT TGTCAGGAGT GCACCTCTCT ACTTGGGAGG TACAATTGCC

2851 ATATGATTTC TAGCTGCCAT GGTGGTTAGG AATGTGATAC TGCCTGTTTG

2901 CAAAGTCACA GACCTTGCCT CAGAAGGAGC TGTGAGCCAG TATTCATTTA

2951 AGAGAATTCC ACCACACTGG CGGCCCGCGC TTGAT  (SEQ ID NO:3)

FIG.4C

```
    GCGGGCCGCCAGTGTGGTGGAATTCGGCTTGTCACTAGGAGAACATTTGTGTTAATTGCA
  1 ---------+---------+---------+---------+---------+---------+  60
    CGCCCGGCGGTCACACCACCTTAAGCCGAACAGTGATCCTCTTGTAAACACAATTAACGT

CTGTGCTCTGTCAAGGAAACTTTGATTTATAGCTGGGGTGCACAAATAATGGTTGCCGGT
 61 ---------+---------+---------+---------+---------+---------+ 120
    GACACGAGACAGTTCCTTTGAAACTAAATATCGACCCCACGTGTTTATTACCAACGGCCA

CGCACATGGATTCGGTAGAACTTTGCCTTCCTGAATCTTTTTCCCTGCACTACGAGGAAG
121 ---------+---------+---------+---------+---------+---------+ 180
    GCGTGTACCTAAGCCATCTTGAAACGGAAGGACTTAGAAAAAGGGACGTGATGCTCCTTC
      M  D  S  V  E  L  C  L  P  E  S  F  S  L  H  Y  E  E  E

AGCTTCTCTGCAGAATGTCAAACAAAGATCGACACATTGATTCCAGCTGTTCGTCCTTCA
181 ---------+---------+---------+---------+---------+---------+ 240
    TCGAAGAGACGTCTTACAGTTTGTTTCTAGCTGTGTAACTAAGGTCGACAAGCAGGAAGT
     L  L  C  R  M  S  N  K  D  R  H  I  D  S  S  C  S  S  F  I

TCAAGACGGAACCTTCCAGCCCAGCCTCCCTGACGGACAGCGTCAACCACCACAGCCCTG
241 ---------+---------+---------+---------+---------+---------+ 300
    AGTTCTGCCTTGGAAGGTCGGGTCGGAGGGACTGCCTGTCGCAGTTGGTGGTGTCGGGAC
     K  T  E  P  S  S  P  A  S  L  T  D  S  V  N  H  H  S  P  G

GTGGCTCTTCAGACGCCAGTGGGAGCTACAGTTCAACCATGAATGGCCATCAGAACGGAC
301 ---------+---------+---------+---------+---------+---------+ 360
    CACCGAGAAGTCTGCGGTCACCCTCGATGTCAAGTTGGTACTTACCGGTAGTCTTGCCTG
     G  S  S  D  A  S  G  S  Y  S  S  T  M  N  G  H  Q  N  G  L

TTGACTCGCCACCTCTCTACCCTTCTGCTCCTATCCTGGGAGGTAGTGGGCCTGTCAGGA
361 ---------+---------+---------+---------+---------+---------+ 420
    AACTGAGCGGTGGAGAGATGGGAAGACGAGGATAGGACCCTCCATCACCCGGACAGTCCT
     D  S  P  P  L  Y  P  S  A  P  I  L  G  G  S  G  P  V  R  K
```

FIG.5A

```
     AACTGTATGATGACTGCTCCAGCACCATTGTTGAAGATCCCCAGACCAAGTGTGAATACA
421  ------------+---------+---------+---------+---------+---------+ 480
     TTGACATACTACTGACGAGGTCGTGGTAACAACTTCTAGGGGTCTGGTTCACACTTATGT
      L  Y  D  D  C  S  S  T  I  V  E  D  P  Q  T  K  C  E  Y  M

TGCTCAACTCGATGCCCAAGAGACTGTGTTTAGTGTGTGGTGACATCGCTTCTGGGTACC
481  ------------+---------+---------+---------+---------+---------+ 540
     ACGAGTTGAGCTACGGGTTCTCTGACACAAATCACACACCACTGTAGCGAAGACCCATGG
      L  N  S  M  P  K  R  L  C  L  V  C  G  D  I  A  S  G  Y  H

ACTATGGGGTAGCATCATGTGAAGCCTGCAAGGCATTCTTCAAGAGGACAATTCAAGGCA
541  ------------+---------+---------+---------+---------+---------+ 600
     TGATACCCCATCGTAGTACACTTCGGACGTTCCGTAAGAAGTTCTCCTGTTAAGTTCCGT
      Y  G  V  A  S  C  E  A  C  K  A  F  F  K  R  T  I  Q  G  N

ATATAGAATACAGCTGCCCTGCCACGAATGAATGTGAAATCACAAAGCGCAGACGTAAAT
601  ------------+---------+---------+---------+---------+---------+ 660
     TATATCTTATGTCGACGGGACGGTGCTTACTTACACTTTAGTGTTTCGCGTCTGCATTTA
      I  E  Y  S  C  P  A  T  N  E  C  E  I  T  K  R  R  R  K  S

CCTGCCAGGCTTGCCGCTTCATGAAGTGTTTAAAAGTGGGCATGCTGAAAGAAGGGGTGC
661  ------------+---------+---------+---------+---------+---------+ 720
     GGACGGTCCGAACGGCGAAGTACTTCACAAATTTTCACCCGTACGACTTTCTTCCCCACG
      C  Q  A  C  R  F  M  K  C  L  K  V  G  M  L  K  E  G  V  R

GTCTTGACAGAGTACGTGGAGGTCGGCAGAAGTACAAGCGCAGGATAGATGCGGAGAACA
721  ------------+---------+---------+---------+---------+---------+ 780
     CAGAACTGTCTCATGCACCTCCAGCCGTCTTCATGTTCGCGTCCTATCTACGCCTCTTGT
      L  D  R  V  R  G  G  R  Q  K  Y  K  R  R  I  D  A  E  N  S

GCCCATACCTGAACCCTCAGCTGGTTCAGCCAGCCAAAAAGCCATATAACAAGATTGTCT
781  ------------+---------+---------+---------+---------+---------+ 840
     CGGGTATGGACTTGGGAGTCGACCAAGTCGGTCGGTTTTTCGGTATATTGTTCTAACAGA
      P  Y  L  N  P  Q  L  V  Q  P  A  K  K  P  Y  N  K  I  V  S
```

FIG.5B

```
     CACATTTGTTGGTGGCTGAACCGGAGAAGATCTATGCCATGCCTGACCCTACTGTCCCCG
841  ---------+---------+---------+---------+---------+---------+ 900
     GTGTAAACAACCACCGACTTGGCCTCTTCTAGATACGGTACGGACTGGGATGACAGGGGC
      H  L  L  V  A  E  P  E  K  I  Y  A  M  P  D  P  T  V  P  D

ACAGTGACATCAAAGCCCTCACTACACTGTGTGACTTGGCCGACCGAGAGTTGGTGGTTA
901  ---------+---------+---------+---------+---------+---------+ 960
     TGTCACTGTAGTTTCGGGAGTGATGTGACACACTGAACCGGCTGGCTCTCAACCACCAAT
      S  D  I  K  A  L  T  T  L  C  D  L  A  D  R  E  L  V  V  I

TCATTGGATGGGCGAAGCATATTCCAGGCTTCTCCACGCTGTCCCTGGCGGACCAGATGA
961  ---------+---------+---------+---------+---------+---------+ 1020
     AGTAACCTACCCGCTTCGTATAAGGTCCGAAGAGGTGCGACAGGGACCGCCTGGTCTACT
      I  G  W  A  K  H  I  P  G  F  S  T  L  S  L  A  D  Q  M  S

GCCTTCTGCAGAGTGCTTGGATGGAAATTTTGATCCTTGGTGTCGTATACCGGTCTCTTT
1021 ---------+---------+---------+---------+---------+---------+ 1080
     CGGAAGACGTCTCACGAACCTACCTTTAAAACTAGGAACCACAGCATATGGCCAGAGAAA
      L  L  Q  S  A  W  M  E  I  L  I  L  G  V  V  Y  R  S  L  S

CATTTGAGGATGAACTTGTCTATGCAGACGATTATATAATGGACGAAGACCAGTCCAAAT
1081 ---------+---------+---------+---------+---------+---------+ 1140
     GTAAACTCCTACTTGAACAGATACGTCTGCTAATATATTACCTGCTTCTGGTCAGGTTTA
      F  E  D  E  L  V  Y  A  D  D  Y  I  M  D  E  D  Q  S  K  L

TAGCAGGCCTTCTTGATCTAAATAATGCTATCCTGCAGCTGGTAAAGAAATACAAGAGCA
1141 ---------+---------+---------+---------+---------+---------+ 1200
     ATCGTCCGGAAGAACTAGATTTATTACGATAGGACGTCGACCATTTCTTTATGTTCTCGT
      A  G  L  L  D  L  N  N  A  I  L  Q  L  V  K  K  Y  K  S  M

TGAAGCTGGAAAAAGAAGAATTTGTCACCCTCAAAGCTATAGCTCTTGCTAATTCAGACT
1201 ---------+---------+---------+---------+---------+---------+ 1260
     ACTTCGACCTTTTTCTTCTTAAACAGTGGGAGTTTCGATATCGAGAACGATTAAGTCTGA
      K  L  E  K  E  E  F  V  T  L  K  A  I  A  L  A  N  S  D  S
```

FIG.5C

```
         CCATGCACATAGAAGATGTTGAAGCCGTTCAGAAGCTTCAGGATGTCTTACATGAAGCGC
1261     ---------+---------+---------+---------+---------+---------+ 1320
         GGTACGTGTATCTTCTACAACTTCGGCAAGTCTTCGAAGTCCTACAGAATGTACTTCGCG
          M  H  I  E  D  V  E  A  V  Q  K  L  Q  D  V  L  H  E  A  L

TGCAGGATTATGAAGCTGGCCAGCACATGGAAGACCCTCGTCGAGCTGGCAAGATGCTGA
1321     ---------+---------+---------+---------+---------+---------+ 1380
         ACGTCCTAATACTTCGACCGGTCGTGTACCTTCTGGGAGCAGCTCGACCGTTCTACGACT
          Q  D  Y  E  A  G  Q  H  M  E  D  P  R  R  A  G  K  M  L  M

TGACACTGCCACTCCTGAGGCAGACCTCTACCAAGGCCGTGCAGCATTTCTACAACATCA
1381     ---------+---------+---------+---------+---------+---------+ 1440
         ACTGTGACGGTGAGGACTCCGTCTGGAGATGGTTCCGGCACGTCGTAAAGATGTTGTAGT
          T  L  P  L  L  R  Q  T  S  T  K  A  V  Q  H  F  Y  N  I  K

AACTAGAAGGCAAAGTCCCAATGCACAAACTTTTTTTGGAAATGTTGGAGGCCAAGGTCT
1441     ---------+---------+---------+---------+---------+---------+ 1500
         TTGATCTTCCGTTTCAGGGTTACGTGTTTGAAAAAAACCTTTACAACCTCCGGTTCCAGA
          L  E  G  K  V  P  M  H  K  L  F  L  E  M  L  E  A  K  V  *
         (SEQ NO ID:4)

GACTAAAAGCTCCCTGGGCCTTCCCATCCTTCATGTTGAAAAAGGGAAAATAAACCCAAG
1501     ---------+---------+---------+---------+---------+---------+ 1560
         CTGATTTTCGAGGGACCCGGAAGGGTAGGAAGTACAACTTTTTCCCTTTTATTTGGGTTC

AGTGATGTCGAAGAAACTTAGAGTTTAGTTAACAACATCAAAAATCAACAGACTGCACTG
1561     ---------+---------+---------+---------+---------+---------+ 1620
         TCACTACAGCTTCTTTGAATCTCAAATCAATTGTTGTAGTTTTTAGTTGTCTGACGTGAC

ATAATTTAGCAGCAAGACTATGAAGCAGCTTTCAGATTCCTCCATAGGTTCCTGATGAGT
1621     ---------+---------+---------+---------+---------+---------+ 1680
         TATTAAATCGTCGTTCTGATACTTCGTCGAAAGTCTAAGGAGGTATCCAAGGACTACTCA
```

FIG. 5D

```
     TCTTTCTACTTTCTCCATCATCTTCTTTCCTCTTTCTTCCCACATTTCTCTTTCTCTTTA
1681 ---------+---------+---------+---------+---------+---------+ 1740
     AGAAAGATGAAAGAGGTAGTAGAAGAAAGGAGAAAGAAGGGTGTAAAGAGAAAGAGAAAT

TTTTTTCTCCTTTTCTTCTTTCACCTCCCTTATTTCTTTGCTTCTTTCATTCCTAGTTCC
1741 ---------+---------+---------+---------+---------+---------+ 1800
     AAAAAAGAGGAAAAGAAGAAAGTGGAGGGAATAAAGAAACGAAGAAAGTAAGGATCAAGG

CATTCTCCTTTATTTTCTTCCCGTCTGCCTGCCTTCTTTCTTTTCTTTACCTACTCTCAT
1801 ---------+---------+---------+---------+---------+---------+ 1860
     GTAAGAGGAAATAAAAGAAGGGCAGACGGACGGAAGAAAGAAAAGAAATGGATGAGAGTA

TCCTCTCTTTTCTCATCCTTCCCCTTTTTTCTAAATTTGAAATAGCTTTAGTTTAAAAAA
1861 ---------+---------+---------+---------+---------+---------+ 1920
     AGGAGAGAAAAGAGTAGGAAGGGGAAAAAAGATTTAAACTTTATCGAAATCAAATTTTTT

AAAAATCCTCCCTTCCCCCTTTCCTTTCCCTTTCTTTCCTTTTTCCCTTTCCTTTTCCCT
1921 ---------+---------+---------+---------+---------+---------+ 1980
     TTTTTAGGAGGGAAGGGGGAAAGGAAAGGGAAAGAAAGGAAAAAGGGAAAGGAAAAGGGA

TTCCTTTCCTTTCCTCTTGACCTTCTTTCCATCTTTCTTTTTCTTCCTTCTGCTGCTGAA
1981 ---------+---------+---------+---------+---------+---------+ 2040
     AAGGAAAGGAAAGGAGAACTGGAAGAAAGGTAGAAAGAAAAAGAAGGAAGACGACGACTT
```

FIG.5E

```
      CTTTTAAAAGAGGTCTCTAACTGAAGAGAGATGGAAGCCAGCCCTGCCAAAGGATGGAGA
2041  ----------+---------+---------+---------+---------+---------+ 2100
      GAAAATTTTCTCCAGAGATTGACTTCTCTCTACCTTCGGTCGGGACGGTTTCCTACCTCT

TCCATAATATGGATGCCAGTGAACTTATTGTGAACCATACCGTCCCCAATGACTAAGGAA
2101  ----------+---------+---------+---------+---------+---------+ 2160
      AGGTATTATACCTACGGTCACTTGAATAACACTTGGTATGGCAGGGGTTACTGATTCCTT

TCAAAGAGAGAGAACCAACGTTCCTAAAAGTACAGTGCAACATATACAAATTGACTGAGT
2161  ----------+---------+---------+---------+---------+---------+ 2220
      AGTTTCTCTCTCTTGGTTGCAAGGATTTTCATGTCACGTTGTATATGTTTAACTGACTCA

GCAGTATTAGATTTCATGGGAGCAGCCTCTAATTAGACAACTTAAGCAACGTTGCATCGG
2221  ----------+---------+---------+---------+---------+---------+ 2280
      CGTCATAATCTAAAGTACCCTCGTCGGAGATTAATCTGTTGAATTCGTTGCAACGTAGCC

CTGCTTCTTATCATTGCTTTTCCATCTAGATCAGTTACAGCCATTTGATTCCTTAATTGT
2281  ----------+---------+---------+---------+---------+---------+ 2340
      GACGAAGAATAGTAACGAAAAGGTAGATCTAGTCAATGTCGGTAAACTAAGGAATTAACA
```

FIG.5F

```
      TTTTTCAAGTCTTCCAGGTATTTGTTAGTTTAGCTACTATGTAACTTTTTCAGGGAATAG
2341  ---------+---------+---------+---------+---------+---------+ 2400
      AAAAAGTTCAGAAGGTCCATAAACAATCAAATCGATGATACATTGAAAAAGTCCCTTATC

TTTAAGCTTTATTCATTCATGCAATACTAAAGAGAAATAAGAATACTGCAATTTTGTGCT
2401  ---------+---------+---------+---------+---------+---------+ 2460
      AAATTCGAAATAAGTAAGTACGTTATGATTTCTCTTTATTCTTATGACGTTAAAACACGA

GGCTTTGAACAATTACGAACAATAATGAAGGACAAATGAATCCTGAAGGAAGATTTTTAA
2461  ---------+---------+---------+---------+---------+---------+ 2520
      CCGAAACTTGTTAATGCTTGTTATTACTTCCTGTTTACTTAGGACTTCCTTCTAAAAATT

AAATGTTTTGTTTCTTCTTACAAATGGAGATTTTTTTGTACCAGCTTTACCACTTTTCAG
2521  ---------+---------+---------+---------+---------+---------+ 2580
      TTTACAAAACAAAGAAGAATGTTTACCTCTAAAAAAACATGGTCGAAATGGTGAAAAGTC

CCATTTATTAATATGGGAATTTAACTTACTCAAGCAATAGTTGAAGGGAAGGTGCATATT
2581  ---------+---------+---------+---------+---------+---------+ 2640
      GGTAAATAATTATACCCTTAAATTGAATGAGTTCGTTATCAACTTCCCTTCCACGTATAA

ATCACGGATGCAATTTATGTTGTGTGCCAGTCTGGTCCCAAACATCAATTTCTTAACATG
2641  ---------+---------+---------+---------+---------+---------+ 2700
      TAGTGCCTACGTTAAATACAACACACGGTCAGACCAGGGTTTGTAGTTAAAGAATTGTAC

AGCTCCAGTTTACCTAAATGTTCACTGACACAAAGGATGAGATTACACCTACAGTGACTC
2701  ---------+---------+---------+---------+---------+---------+ 2760
      TCGAGGTCAAATGGATTTACAAGTGACTGTGTTTCCTACTCTAATGTGGATGTGCCTGAG
```

FIG.5G

```
            TGAGTAGTCACATATATAAGCACTGCACATGAGATATAGATCCGTAGAATTGTCAGGAGT
2761    ----------+---------+---------+---------+---------+---------+  2820
            ACTCATCAGTGTATATATTCGTGACGTGTACTCTATATCTAGGCATCTTAACAGTCCTCA

GCACCTCTCTACTTGGGAGGTACAATTGCCATATGATTTCTAGCTGCCATGGTGGTTAGG
2821    ----------+---------+---------+---------+---------+---------+  2880
            CGTGGAGAGATGAACCCTCCATGTTAACGGTATACTAAAGATCGACGGTACCACCAATCC

AATGTGATACTGCCTGTTTGCAAAGTCACAGACCTTGCCTCAGAAGGAGCTGTGAGCCAG
2881    ----------+---------+---------+---------+---------+---------+  2940
            TTACACTATGACGGACAAACGTTTCAGTGTCTGGAACGGAGTCTTCCTCGACACTCGGTC

TATTCATTTAAGAGAATTCCACCACACTGGCGGCCCGCGCTTGAT  (SEQ ID NO:3)
2941    ----------+---------+---------+---------+-----                  2985
            ATAAGTAAATTCTCTTAAGGTGGTGTGACCGCCGGGCGCGAACTA  (SEQ ID NO:30)
```

FIG.5H

1   MDSVELCLPE SFSLHYEEEL LCRMSNKDRH IDSSCSSFIK TEPSSPASLT

51  DSVNHHSPGG SSDASGSYSS TMNGHQNGLD SPPLYPSAPI LGGSGPVRKL

101 YDDCSSTIVE DPQTKCEYML NSMPKRL<u>CLV CGDIASGYHY GVASCEACKA</u>

151 <u>FFKPTIQGNI EYSCPATNEC EITKRRRKSC QACRFMKCLK VGM</u>LKEGVRL

201 DRVRGGRQKY KRRIDAENSP YLNPQLVQPA KKPYNKIVSH LLVAEPEKIY

251 AMPDPTVPDS DIKALTTLCD LADRELVVII GWAKHIPGFS TLSLADQMSL

301 LQSAWMEILI LGVVYRSLSF EDELVYADDY IMDEDQSKLA GLLDLNNAIL

351 QLVKKYKSMK LEKEEFVTLK AIALANSDSM HIEDVEAVQK LQDVLHEALQ

401 DYEAGQHMED PRRAGKMLMT LPLLEQTSTK AVQHFYNIKL EGKVPMHKLF

451 LEMLEAKV* (SEQ ID NO:4)

FIG. 6

```
   1 GCGGGCCGCC AGTGTGGTGG AATTCGGCTT GTCACTAGGA GAACATTTGT
  51 GTTAATTGCA CTGTGCTCTG TCAAGGAAAC TTTGATTTAT AGCTGGGGTG
 101 CACAAATAAT GGTTGCCGGT CGCACATGGA TTCGGTAGAA CTTTGCCTTC
 151 CTGAATCTTT TTCCCTGCAC TACGAGGAAG AGCTTCTCTG CAGAATGTCA
 201 AACAAAGATC GACACATTGA TTCCAGCTGT TCGTCCTTCA TCAAGACGGA
 251 ACCTTCCAGC CCAGCCTCCC TGACGGACAG CGTCAACCAC CACAGCCCTG
 301 GTGGCTCTTC AGACGCCAGT GGGAGCTACA GTTCAACCAT GAATGGCCAT
 351 CAGAACGGAC TTGACTCGCC ACCTCTCTAC CCTTCTGCTC CTATCCTGGG
 401 AGGTAGTGGG CCTGTCAGGA AACTGTATGA TGACTGCTCC AGCACCATTG
 451 TTGAAGATCC CCAGACCAAG TGTGAATACA TGCTCAACTC GATGCCCAAG
 501 AGACTGTGTT TAGTGTGTGG TGACATCGCT TCTGGGTACC ACTATGGGGT
 551 AGCATCATGT GAAGCCTGCA AGGCATTCTT CAAGAGGACA ATTCAAGGCA
 601 ATATAGAATA CAGCTGCCCT GCCACGAATG AATGTGAAAT CACAAAGCGC
 651 AGACGTAAAT CCTGCCAGGC TTGCCGCTTC ATGAAGTGTT TAAAAGTGGG
 701 CATGCTGAAA GAAGGGGTGC GTCTTGACAG AGTACGTGGA GGTCGGCAGA
 751 AGTACAAGCG CAGGATAGAT GCGGAGAACA GCCCATACCT GAACCCTCAG
 801 CTGGTTCAGC CAGCCAAAAA GCCATATAAC AAGATTGTCT CACATTTGTT
 851 GGTGGCTGAA CCGGAGAAGA TCTATGCCAT GCCTGACCCT ACTGTCCCCG
 901 ACAGTGACAT CAAAGCCCTC ACTACACTGT GTGACTTGGC CGACCGAGAG
 951 TTGGTGGTTA TCATTGGATG GGCGAAGCAT ATTCCAGGCT TCTCCACGCT
1001 GTCCCTGGCG GACCAGATGA GCCTTCTGCA GAGTGCTTGG ATGGAAATTT
```

FIG.7A

```
1051  TGATCCTTGG TGTCGTATAC CGGTCTCTTT CATTTGAGGA TGAACTTGTC

1101  TATGCAGACG ATTATATAAT GGACGAAGAC CAGTCCAAAT TAGCAGGCCT

1151  TCTTGATCTA AATAATGCTA TCCTGCAGCT GGTAAAGAAA TACAAGAGCA

1201  TGAAGCTGGA AAAAGAAGAA TTTGTCACCC TCAAAGCTAT AGCTCTTGCT

1251  AATTCAGACT CCATGCACAT AGAAGATGTT GAAGCCGTTC AGAAGCTTCA

1301  GGATGTCTTA CATGAAGCGC TGCAGGATTA TGAAGCTGGC CAGCACATGG

1351  AGAAGACCCT CGTCGAGCTG GCAAGATGCT GATGACACTG CCACTCCTGA

1401  GGCAGACCTC TACCAAGGCC GTGCAGCATT TCTACAACAT CAAACTAGAA

1451  GGCAAAGTCC CAATGCACAA ACTTTTTTTG GAAATGTTGG AGGCCAAGGT

1501  CTGACTAAAA GCTCCCTGGG CCTTCCCATC CTTCATGTTG AAAAAGGGAA

1551  AATAAACCCA AGAGTGATGT CGAAGAAACT TAGAGTTTAG TTAACAACAT

1601  CAAAAATCAA CAGACTGCAC TGATAATTTA GCAGCAAGAC TATGAAGCAG

1651  CTTTCAGATT CCTCCATAGG TTCCTGATGA GTTCTTTCTA CTTTCTCCAT

1701  CATCTTCTTT CCTCTTTCTT CCCACATTTC TCTTTCTCTT TATTTTTTCT

1751  CCTTTTCTTC TTTCACCTCC CTTATTTCTT TGCTTCTTTC ATTCCTAGTT

1801  CCCATTCTCC TTTATTTTCT TCCCGTCTGC CTGCCTTCTT TCTTTTCTTT

1851  ACCTACTCTC ATTCCTCTCT TTTCTCATCC TTCCCCTTTT TTCTAAATTT

1901  GAAATAGCTT TAGTTTAAAA AAAAAAATCC TCCCTTCCCC CTTTCCTTTC

1951  CCTTTCTTTC CTTTTTCCCT TTCCTTTTCC CTTTCCTTTC CTTTCCTCTT

2001  GACCTTCTTT CCATCTTTCT TTTTCTTCCT TCTGCTGCTG AACTTTTAAA

2051  AGAGGTCTCT AACTGAAGAG AGATGGAAGC CAGCCCTGCC AAAGGATGGA
```

FIG. 7B

```
2101  GATCCATAAT ATGGATGCCA GTGAACTTAT TGTGAACCAT ACCGTCCCCA

2151  ATGACTAAGG AATCAAAGAG AGAGAACCAA CGTTCCTAAA AGTACAGTGC

2201  AACATATACA AATTGACTGA GTGCAGTATT AGATTTCATG GGAGCAGCCT

2251  CTAATTAGAC AACTTAAGCA ACGTTGCATC GGCTGCTTCT TATCATTGCT

2301  TTTCCATCTA GATCAGTTAC AGCCATTTGA TTCCTTAATT GTTTTTTCAA

2351  GTCTTCCAGG TATTTGTTAG TTTAGCTACT ATGTAACTTT TTCAGGGAAT

2401  AGTTTAAGCT TTATTCATTC ATGCAATACT AAAGAGAAAT AAGAATACTG

2451  CAATTTTGTG CTGGCTTTGA ACAATTACGA ACAATAATGA AGGACAAATG

2501  AATCCTGAAG GAAGATTTTT AAAAATGTTT TGTTTCTTCT TACAAATGGA

2551  GATTTTTTTG TACCAGCTTT ACCACTTTTC AGCCATTTAT TAATATGGGA

2601  ATTTAACTTA CTCAAGCAAT AGTTGAAGGG AAGGTGCATA TTATCACGGA

2651  TGCAATTTAT GTTGTGTGCC AGTCTGGTCC CAAACATCAA TTTCTTAACA

2701  TGAGCTCCAG TTTACCTAAA TGTTCACTGA CACAAAGGAT GAGATTACAC

2751  CTACAGTGAC TCTGAGTAGT CACATATATA AGCACTGCAC ATGAGATATA

2801  GATCCGTAGA ATTGTCAGGA GTGCACCTCT GTACTTGGGA GGTACAATTG

2851  CCATATGATT TCTAGCTGCC ATGGTGGTTA GGAATGTGAT ACTGCCTGTT

2901  TGCAAAGTCA CAGACCTTGC CTCAGAAGGA GCTGTGAGCC AGTATTCATT

2951  TAAGAGAATT CCACCACACT GGCGGCCCGC GCTTGAT (SEQ ID NO:5)
```

FIG.7C

```
  1  MDSVELCLPE SFSLHYEEEL LCRMSNKDRH IDSSCSSFIK TEPSSPASLT

51  DSVNHHSPGG SSDASGSYSS TMNGHQNGLD SPPLYPSAPI LGGSGPVRKL

101  TDDCSSTIVE DPQTKCEYML NSMPKRLCLV CGDIASGYHY GVASCEACKA

151  FFKRTIQGNI IYSCPATNEC EITKRRRKSC QACRFMKCLK VGMLKEGVRL

201  DRVRGGRQKY KRRIDAENSP YLNPQLVQPA KKPYNKIVSH LLVAEPEKIY

251  AMPDPTVPDS DIKALTTLCD LADRELVVII GWAKHIPGFS TLSLADQMSL

301  LQSAWMEILI LGVVYRSLSF EDELVYADDY IMDEDQSKLA GLLDLNNAIL

351  QLVKKYKSMK LEKEEFVTLK AIALANSDSM HIEDVEAVQK LQDVLHEALQ

401  DYEAGQHMEK TLVELARC*  (SEQ ID NO:6)
```

FIG. 8

DNA MOLECULES ENCODING HUMAN NUCLEAR RECEPTOR PROTEINS

CROSS-REFERENCE TO RELATED APPLICATIONS

This application is a continuation of U.S. Provisional Application Ser. No. 60/078,633, filed Mar. 19, 1998 which is a continuation-in-part of U.S. Provisional Application Ser. No. 60/062,902, filed Oct. 21, 1997, which is a continuation-in-part of U.S. Provisional Application Ser. No. 60/057,090, filed Aug. 27, 1997.

STATEMENT REGARDING FEDERALLY-SPONSORED R&D

Not applicable

REFERENCE TO MICROFICHE APPENDIX

Not applicable.

FIELD OF THE INVENTION

The present invention relates in part to isolated nucleic acid molecules (polynucleotide) which encode human nuclear receptor proteins, referred to throughout as nNR1, nNR2 and/or nNR2-1. The present invention also relates to recombinant vectors and recombinant hosts which contain a DNA fragment encoding nNR1, nNR2 and/or nNR2-1, substantially purified forms of associated human nNR1, nNR2 and/or nNR2-1 protein, human mutant proteins, and methods associated with identifying compounds which modulate nNR1, nNR2 and/or nNR2-1 activity.

BACKGROUND OF THE INVENTION

The nuclear receptor superfamily, which includes steroid hormone receptors, are small chemical ligand-inducible transcription factors which have been shown to play roles in controlling development, differentiation and physiological function. Isolation of cDNA clones encoding nuclear receptors reveal several characteristics. First, the $NH_2$-terminal regions, which vary in length between receptors, is hypervariable with low homology between family members. There are three internal regions of conservation, referred to as domain I, II and III. Region I is a cysteine-rich region which is referred to as the DNA binding domain (DBD). Regions II and III are within the COOH-terminal region of the protein and is also referred to as the ligand binding domain (LBD). For a review, see Power et al. (1992, *Trends in Pharmaceutical Sciences* 13: 318–323).

The lipophilic hormones that activate steroid receptors are known to be associated with human diseases. Therefore, the respective nuclear receptors have been identified as possible targets for therapeutic intervention. For a review of the mechanism of action of various steroid hormone receptors, see Tsai and O'Malley (1994, *Annu. Rev. Biochem.* 63:451–486).

Recent work with non-steroid nuclear receptors has also shown the potential as drug targets for therapeutic intervention. This work reports that peroxisome proliferator activated receptor g (PPARg), identified by a conserved DBD region, promotes adipocyte differentiation upon activation and that thiazolidinediones, a class of antidiabetic drugs, function through PPARg (Tontonoz et al., 1994, *Cell* 79: 1147–1156; Lehmann et al., 1995, *J. Biol. Chem.* 270(22): 12953–12956; Teboul et al., 1995, *J. Biol. Chem.* 270(47): 28183–28187). This indicates that PPARg plays a role in glucose homeostasis and lipid metabolism.

Giguère, et al. (1988, *Nature* 331: 91–94) isolated two cDNAs which encode a human nuclear receptor, referred to as hERR1 and hEER2. The authors did not assign a ligand and subsequent ligand-inducible function to either of these human nuclear receptors.

Trapp and Holsboer (1996, *J. Biol. Chem.* 271(17): 9879–9882) show that hERR2 acts as a cell-specific inhibitor of glucocorticoid receptor-mediated gene expression.

It would be advantageous to identify a gene encoding an additional human nuclear receptor protein. A nucleic acid molecule expressing a human nuclear receptor protein will be useful in screening for compounds acting as a modulator of cell differentiation, cell development and physiological function. The present invention addresses and meets these needs by disclosing isolated nucleic acid molecules which express a human nuclear receptor protein which will have a role in cell differentiation and development.

SUMMARY OF THE INVENTION

The present invention relates to isolated nucleic acid molecules (polynucleotides) which encode novel nuclear receptor proteins, preferably human nuclear receptor proteins, such as human nuclear receptor proteins exemplified and referred to throughout this specification as nNR1, nNR2 and/or nNR2-1.

The present invention also relates to isolated nucleic acid fragments of nNR1 (SEQ ID NO:1) and nNR2 (SEQ ID NO:3) which encode mRNA expressing a biologically active novel human nuclear receptor. Any such nucleic acid fragment will encode either a protein or protein fragment comprising at least an intracellular DNA-binding domain and/or ligand binding domain, domains conserved throughout the human nuclear receptor family domain which exist in nNR1 (SEQ ID NO:2) and nNR2 (SEQ ID NO:4). Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for nNR1, nNR2 and/or nNR2-1 function.

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified nucleic acid molecules disclosed throughout this specification.

A preferred aspect of the present invention is disclosed in FIGS. 1A–C and SEQ ID NO:1, a human cDNA encoding a novel nuclear trans-acting receptor protein, nNR1.

Another preferred aspect of the present invention is disclosed in FIGS. 4A–C and SEQ ID NO:3, a human cDNA encoding a novel nuclear trans-acting receptor protein, nNR2.

Another preferred aspect of the present invention is disclosed in FIGS. 7A–C and SEQ ID NO:5, a human cDNA encoding a truncated version of nNR2, referred to as nNR2-1.

The present invention also relates to a substantially purified form of the novel nuclear trans-acting receptor protein, nNR1, which is disclosed in FIGS. 2A–F and FIG. 3 and as set forth in SEQ ID NO:2.

The present invention also relates to biologically active fragments and/or mutants of nNR1 as set forth as SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists of nNR1 function.

The present invention also relates to a substantially purified form of the novel nuclear trans-acting receptor protein, nNR2, which is disclosed in FIGS. 5A–E and FIG. 6 and as set forth in SEQ ED NO:4.

The present invention also relates to biologically active fragments and/or mutants of nNR2 as set forth as SEQ ID NO:4, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists of nNR2 function.

A preferred aspect of the present invention is disclosed in FIG. 3 and is set forth as SEQ ID NO:2, the amino acid sequence of the novel nuclear trans-acting receptor protein, nNR1.

A preferred aspect of the present invention is disclosed in FIG. 6 and is set forth as SEQ ID NO:4, the amino acid sequence of the novel nuclear trans-acting receptor protein, nNR2.

A preferred aspect of the present invention is disclosed in FIG. 8 and is set forth as SEQ ID NO:6, the amino acid sequence of a truncated version of nNR2, referred to as nNR2-1.

The present invention also relates to polyclonal and monoclonal antibodies raised in response to either the human form of nNR1, nNR2 and/or nNR2-1 disclosed herein, or a biologically active fragment thereof. It will be especially preferable to raise antibodies against epitopes within the NH$_2$-terminal domain of nNR1, nNR2 and/or nNR2-1, which show the least homology to other known proteins belonging to the human nuclear receptor superfamily. To this end, the DNA molecules, RNA molecules, recombinant protein and antibodies of the present invention may be used to screen and measure levels of human nNR1, nNR2 and/or nNR2-1. The recombinant proteins, DNA molecules, RNA molecules and antibodies lend themselves to the formulation of kits suitable for the detection and typing of human nNR1, nNR2 and/or nNR2-1.

The present invention also relates to isolated nucleic acid molecules which are fusion constructions expressing fusion proteins useful in assays to identify compounds which modulate wild-type human nNR1, nNR2 and/or nNR2-1 activity. A preferred aspect of this portion of the invention includes, but is not limited to, glutathione S-transferase GST-nNR1 and/or GST-nNR2 fusion constructs. These fusion constructs include, but are not limited to, all or a portion of the ligand-binding domain of nNR1, nNR2 and/or nNR2-1, respectively, as an in-frame fusion at the carboxy terminus of the GST gene. The disclosure of SEQ ID NOS:1–4 allow the artisan of ordinary skill to construct any such nucleic acid molecule encoding a GST-nuclear receptor fusion protein. Soluble recombinant GST-nuclear receptor fusion proteins may be expressed in various expression systems, including *Spodoptera frugiperda* (Sf21) insect cells (Invitrogen) using a baculovirus expression vector (e.g., Bac-N-Blue DNA from Invitrogen or pAcG2T from Pharmingen).

It is an object of the present invention to provide an isolated nucleic acid molecule which encodes a novel form of a nuclear receptor protein such as human nNR1and/or human nNR2, human nuclear receptor protein fragments of full length proteins such as nNR1, nNR2 and/or nNR2-1, and mutants which are derivatives of SEQ ID NO:2 and SEQ ID NO:4. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for nNR1, nNR2 and/or nNR2-1 function.

It is a further object of the present invention to provide the human nuclear receptor proteins or protein fragments encoded by the nucleic acid molecules referred to in the preceding paragraph.

It is a further object of the present invention to provide recombinant vectors and recombinant host cells which comprise a nucleic acid sequence encoding human nNR1, nNR2 and/or nNR2-1 or a biological equivalent thereof.

It is an object of the present invention to provide a substantially purified form of nNR1, as set forth in SEQ ID NO:2.

It is an object of the present invention to provide for biologically active fragments and/or mutants of nNR1, including but not necessarily limited to amino acid substitutions, deletions, additions, amino terminal truncations and carboxy-terminal truncations such that these mutations provide for proteins or protein fragments of diagnostic, therapeutic or prophylactic use.

It is an object of the present invention to provide a substantially purified form of nNR2, as set forth in SEQ ID NO:4.

It is an object of the present invention to provide for biologically active fragments and/or mutants of nNR2, including but not necessarily limited to amino acid substitutions, deletions, additions, amino terminal truncations and carboxy-terminal truncations such that these mutations provide for proteins or protein fragments of diagnostic, therapeutic or prophylactic use.

It is also an object of the present invention to provide for nNR1-and/or nNR2-based in-frame fusion constructions, methods of expressing these fusion constructions and biological equivalents disclosed herein, related assays, recombinant cells expressing these constructs and agonistic and/or antagonistic compounds identified through the use DNA molecules encoding human nuclear receptor proteins such as nNR1, nNR2 and/or nNR2-1.

As used herein, "DBD" refers to DNA binding domain.

As used herein, "LBD" refers to ligand binding domain.

As used herein, the term "mammalian host" refers to any mammal, including a human being.

BRIEF DESCRIPTION OF THE DRAWINGS

FIGS. 1A–C shows the nucleotide sequence (SEQ ID NO:1) which comprises the open reading frame encoding the human nuclear receptor protein, nNR1.

FIGS. 2A–F shows the nucleotide sequence of the double stranded cDNA molecule (SEQ ID NO:1 and SEQ ID NO:29) which encodes nNR1, and the amino acid sequence of nNR1 (SEQ ID NO:2). The region in bold and underline is the DNA binding domain.

FIG. 3 shows the amino acid sequence of nNR1 (SEQ ID NO:2). The region in bold and underline is the DNA binding domain.

FIGS. 4A–C shows the nucleotide sequence (SEQ ID NO:3) which comprises the open reading frame encoding the human nuclear receptor protein, nNR2.

FIGS. 5A–H shows the nucleotide sequence of the double stranded cDNA molecule (SEQ ID NO:1 and SEQ ID NO:29) which encodes nNR2, and the amino acid sequence of nNR2 (SEQ ID NO:4). The region in bold and underline is the DNA binding domain.

FIG. 6 shows the amino acid sequence of nNR2 (SEQ ID NO:4). The region in bold and underline is the DNA binding domain.

FIGS. 7A–C shows the nucleotide sequence (SEQ ID NO:5) which comprises the open reading frame encoding the human nuclear receptor protein, nNR2.

FIG. 8 shows the amino acid sequence of nNR2-1, a carboxy-terminal truncated version of nNR2 (SEQ ID NO:6). The region in bold and underline is the DNA binding domain.

DETAILED DESCRIPTION OF THE INVENTION

The present invention relates to isolated nucleic acid and protein forms which represent nuclear receptors, preferably but not necessarily limited to human receptors. These expressed proteins are novel nuclear receptors and which are useful in the identification of downstream target genes and ligands regulating their activity. The nuclear receptor superfamily is composed of a group of structurally related receptors which are regulated by chemically distinct ligands. The common structure for a nuclear receptor is a highly conserved DNA binding domain (DBD) located in the center of the peptide and the ligand-binding domain (LBD) at the COOH-terminus. Eight out of the nine non-variant cysteines form two type II zinc fingers which distinguish nuclear receptors from other DNA-binding proteins. The DBDs share at least 50% to 60% amino acid sequence identity even among the most distant members in vertebrates. The superfamily has been expanded within the past decade to contain approximately 25 subfamilies. An EST database search using whole peptide sequences of several representative subfamily members was used to identify two human ESTs (GenBank accession numbers h91890 and w26275 for an EST corresponding to nNR1, nNR2 and/or nNR2-1, respectively). The sequence information from each EST was utilized to isolate and characterize the full length cDNA for the gene corresponding to nNR1 (see FIGS. 1A–C and SEQ ID NO:1) and nNR2 (see FIGS. 4A–C and SEQ ID NO:3). The cDNA of SEQ ID NO:1 encodes nNR1, a protein 500 amino acids in length (FIG. 3; SEQ ID NO:2), which has a distinctive DBD structure (FIGS. 2A–F). The cDNA of SEQ ID NO:3 encodes nNR2, a protein 458 amino acids (FIG. 6; SEQ ED NO:4) in length, and also has a distinctive DBD structure (FIGS. 5A–E). The cDNA of SEQ ID NO:5 encodes nNR2-1, a protein 418 amino acids (FIG. 8; SEQ ID NO:6) in length which is a carboxy terminal truncated version of nNR2. The protein nNR2-1 also has a distinctive DBD structure (FIG. 8).

The nNR1 protein shows 95% homology to hERR2 (Giguère, et al., 1988, *Nature* 331: 91–94) in the overlapping peptide region. However, nNR1 contains an additional 67 amino acids at the carboxy-terminus in comparison to hERR2. The gene encoding nNR1 is located on locus 14q24.3~14q31, which is the Alzheimer disease gene 3 (AD3) locus. Therefore, nNR1 may be an endogenous modulator of glucocorticoid receptor (GR) in view of data showing that hERR2 represses GR activity. nNR2 and nNR2-1 share 77% and 75% homology, respectively, at the amino acid level to hERR2 (Giguère, et al., 1988, *Nature* 331:91–94) in the overlapping region. The nNR2 and nNR1 proteins show 77% homology at the amino acid level. The gene encoding nNR2 is located on chromosome 1. Both genes are expressed at very low levels in the majority of the tissues examined via RT-PCR.

Therefore, the present invention also relates to isolated nucleic acid fragments of nNR1 (SEQ ID NO:1) and nNR2 (SEQ ID NO:3) which encode mRNA expressing a biologically active novel human nuclear receptor. Any such nucleic acid fragment will encode either a protein or protein fragment comprising at least an intracellular DNA-binding domain and/or ligand binding domain, domains conserved throughout the human nuclear receptor family domain which exist in nNR1 (SEQ ID NO:2) and nNR2 (SEQ ID NO:4). Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for nNR1, nNR2 and/or nNR2-1 function. Such a nucleic acid fragment is exemplified as an altered version of the DNA fragment encoding nNR2. This DNA molecule (as set forth in SEQ ID NO:5) is identical to SEQ ID NO:3 save for a two nucleotide insertion at nucleotide 1352 of SEQ ID NO:3. This insertion results in a shifted reading frame and introduction of a TGA termination codon 33 nucleotides from the insertion site, resulting in an open reading frame which encodes the carboxy-truncated nNR2 protein, nNR2-1, as shown in FIG. 8 and SEQ ID NO: 6.

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified nucleic acid molecules disclosed throughout this specification.

A preferred aspect of the present invention is disclosed in FIGS. 1A–C and SEQ ID NO:1, a human cDNA encoding a novel nuclear trans-acting receptor protein, nNR1, disclosed as follows:

(SEQ ID NO:1)

GAATATGATG ACCCTAATGC AACAATATCT AACATACTAT

CCGAGCTTCG GTCATTTGGA AGAACTGCAG ATTTTCCTCC

TTCAAAATTA AAGTCAGGTT ATGGAGAACA TGTATGCTAT

GTTCTTGATT GCTTCGCTGA AGAAGCATTG AAATATATTG

GTTTCACCTG GAAAAGGCCA ATATACCCAG TAGAAGAATT

AGAAGAAGAA AGCGTTGCAG AAGATGATGC AGAATTAACA

TTAAATAAAG TGGATGAAGA ATTTGTGGAA GAAGAGACAG

ATAATGAAGA AAACTTTATT GATCTCAACG TTTTAAAGGC

-continued
```
CCAGACATAT CACTTGGATA TGAACGAGAC TGCCAAACAA

GAAGATATTT TGGAATCCAC AACAGATGCT GCAGAATGGA

GCCTAGAAGT GGAACGTGTA CTACCGCAAC TGAAAGTCAC

GATTAGGACT GACAATAAGG ATTGGAGAAT CCATGTTGAC

CAAATGCACC AGCACAGAAG TGGAATTGAA TCTGCTCTAA

AGGAGACCAA GGGATTTTTG GACAAACTCC ATAATGAAAT

TACTAGGACT TTGGAAAAGA TCAGCAGCCG AGAAAAGTAC

ATCAACAATC AGCCGGGAGC CCATGGAGCA CTGTCCTCAG

AGATGCGCAG GTTAGGCTCA CTGTCTAGGC CAGGCCCACC

TTAGTCACTG TGGACTGGCA ATGGAAGCTC TTCCTGGACA

CACCTGCCCT AGCCCTCACC CTGGGGTGGA AGAGAAATGA

GCTTGGCTTG CAACTCAGAC CATTCCACGG AGGCATCCTC

CCCTTCCCTG GGCTGGTGAA TAAAAGTTTC CTGAGGTCAA

GGACTTCCTT TTCCCTGCCA AAATGGTGTC CAGAACTTTG

AGGCCAGAGG TGATCCAGTG ATTTGGGAGC TGCAGGTCAC

ACAGGCTGCT CAGAGGGCTG CTGAACAGGA TGTCCTCGGA

CGACAGGCAC CTGGGCTCCA GCTGCGGCTC CTTCATCAAG

ACTGAGCCGT CCAGCCCGTC CTCGGGCATA GATGCCCTCA

GCCACCACAG CCCCAGTGGC TCGTCCGACG CCAGCGGCGG

CTTTGGCCTG GCCCTGGGCA CCCACGCCAA CGGTCTGGAC

TCGCCACCCA TGTTTGCAGG CGCCGGGCTG GGAGGCACCC

CATGCCGCAA GAGCTACGAG GACTGTGCCA GCGGCATCAT

GGAGGACTCG GCCATCAAGT GCGAGTACAT GCTCAACGCC

ATCCCCAAGC GCCTGTGCCT CGTGTGCGGG GACATTGCCT

CTGGCTACCA CTACGGCGTG GCCTCCTGCG AGGCTTGCAA

GGCCTTCTTC AAGAGGACTA TCCAAGGGAA CATTGAGTAC

AGCTGCCCGG CCACCAACGA GTGCGAGATC ACCAAACGGA

GGCGCAAGTC CTGCCAGGCC TGCCGCTTCA TGAAATGCCT

CAAAGTGGGG ATGCTGAAGG AAGGTGTGCG CCTTGATCGA

GTGCGTGGAG GCCGTCAGAA ATACAAGCGA CGGCTGGACT

CAGAGAGCAG CCCATACCTG AGCTTACAAA TTTCTCCACC

TGCTAAAAAG CCATTGACCA AGATTGTCTC ATACCTACTG

GTGGCTGAGC CGGACAAGCT CTATGCCATG CCTCCCCCTG

GTATGCCTGA GGGGACATC AAGGCCCTGA CCACTCTCTG

TGACCTGGCA GACCGAGAGC TTGTGGTCAT CATTGGCTGG

GCCAAGCACA TCCCAGGCTT CTCAAGCCTC TCCCTGGGGG

ACCAGATGAG CCTGCTGCAG AGTGCCTGGA TGGAAATCCT

CATCCTGGGC ATCGTGTACC GCTCGCTGCC CTACGACGAC

AAGCTGGTGT ACGCTGAGGA CTACATCATG GATGAGGAGC

ACTCCCGCCT CGCGGGGCTG CTGGAGCTCT ACCGGGCCAT
```

-continued
```
CCTGCAGCTG GTACGCAGGT ACAAGAAGCT CAAGGTGGAG

AAGGAGGAGT TTGTGACGCT CAAGGCCCTG GCCCTCGCCA

ACTCCGATTC CATGTACATC GAGGATCTAG AGGCTGTCCA

GAAGCTGCAG GACCTGCTGC ACGAGGCACT GCAGGACTAC

GAGCTGAGCC AGCGCCATGA GGAGCCCTGG AGGACGGGCA

AGCTGCTGCT GACACTGCCG CTGCTGCGGC AGACGGCCGC

CAAGGCCGTG CAGCACTTCT ATAGCGTCAA ACTGCAGGGC

AAAGTGCCCA TGCACAAACT CTTCCTGGAG ATGCTGGAGG

CCAAGGCCTG GGCCAGGGCT GACTCCCTTC AGGAGTGGAG

GCCACTGGAG CAAGTGCCCT CTCCCCTCCA CCGAGCCACC

AAGAGGCAGC ATGTGCATTT CCTAACTCCC TTGCCCCCTC

CCCCATCTGT GGCCTGGGTG GGCACTGCTC AGGCTGGATA

CCACCTGGAG GTTTTCCTTC CGCAGAGGGC AGGTTGGCCA

AGAGCAGCTT AGAGGATCTC CCAAGGATGA AAGAATGTCA

AGCCATGATG GAAAATGCCC CTTCCAATCA GCTGCCTTCA

CAAGCAGGGA TCAGAGCAAC TCCCCGGGGA TCCCCAATCC

ACGCCCTTCT AGTCCAACCC CCCTCAATGA GAGAGGCAGG

CAGATCTCAC CCAGCACTAG GACACCAGGA GGCCAGGGAA

AGCATCTCTG GCTCACCATG TAACATCTGG CTTGGAGCAA

GTGGGTGTTC TGCACACCAG GCAGCTGCAC CTCACTGGAT

CTAGTGTTGC TGCGAGTGAC CTCACTTCAG AGCCCCTCTA

GCAGAGTGGG GCGGAAGTCC TGATGGTTGG TGTCCATGAG

GTGGAAG.
```

Another preferred aspect of the present invention is disclosed in FIGS. 4A–C and SEQ. ID NO:3, a human cDNA encoding a novel nuclear trans-acting receptor protein, nNR2, disclosed as follows:

(SEQ ID NO:3)
```
GCGGGCCGCC AGTGTGGTGG AATTCGGCTT GTCACTAGGA

GAACATTTGT GTTAATTGCA CTGTGCTCTG TCAAGGAAAC

TTTGATTTAT AGCTGGGGTG CACAAATAAT GGTTGCCGGT

CGCACATGGA TTCGGTAGAA CTTTGCCTTC CTGAATCTTT

TTCCCTGCAC TACGAGGAAG AGCTTCTCTG CAGAATGTCA

AACAAAGATC GACACATTGA TTCCAGCTGT TCGTCCTTCA

TCAAGACGGA ACCTTCCAGC CCAGCCTCCC TGACGGACAG

CGTCAACCAC CACAGCCCTG GTGGCTCTTC AGACGCCAGT

GGGAGCTACA GTTCAACCAT GAATGGCCAT CAGAACGGAC

TTGACTCGCC ACCTCTCTAC CCTTCTGCTC CTATCCTGGG

AGGTAGTGGG CCTGTCAGGA AACTGTATGA TGACTGCTCC

AGCACCATTG TTGAAGATCC CCAGACCAAG TGTGAATACA
```

-continued

```
TGCTCAACTC GATGCCCAAG AGACTGTGTT TAGTGTGTGG
TGACATCGCT TCTGGGTACC ACTATGGGGT AGCATCATGT
GAAGCCTGCA AGGCATTCTT CAAGAGGACA ATTCAAGGCA
ATATAGAATA CAGCTGCCCT GCCACGAATG AATGTGAAAT
CACAAAGCGC AGACGTAAAT CCTGCCAGGC TTGCCGCTTC
ATGAAGTGTT TAAAAGTGGG CATGCTGAAA GAAGGGGTGC
GTCTTGACAG AGTACGTGGA GGTCGGCAGA AGTACAAGCG
CAGGATAGAT GCGGAGAACA GCCCATACCT GAACCCTCAG
CTGGTTCAGC CAGCCAAAAA GCCATATAAC AAGATTGTCT
CACATTTGTT GGTGGCTGAA CCGGAGAAGA TCTATGCCAT
GCCTGACCCT ACTGTCCCCG ACAGTGACAT CAAAGCCCTC
ACTACACTGT GTGACTTGGC CGACCGAGAG TTGGTGGTTA
TCATTGGATG GGCGAAGCAT ATTCCAGGCT TCTCCACGCT
GTCCCTGGCG GACCAGATGA GCCTTCTGCA GAGTGCTTGG
ATGGAAATTT TGATCCTTGG TGTCGTATAC CGGTCTCTTT
CATTTGAGGA TGAACTTGTC TATGCAGACG ATTATATAAT
GGACGAAGAC CAGTCCAAAT TAGCAGGCCT TCTTGATCTA
AATAATGCTA TCCTGCAGCT GGTAAAGAAA TACAAGAGCA
TGAAGCTGGA AAAAGAAGAA TTTGTCACCC TCAAAGCTAT
AGCTCTTGCT AATTCAGACT CCATGCACAT AGAAGATGTT
GAAGCCGTTC AGAAGCTTCA GGATGTCTTA CATGAAGCGC
TGCAGGATTA TGAAGCTGGC CAGCACATGG AAGACCCTCG
TCGAGCTGGC AAGATGCTGA TGACACTGCC ACTCCTGAGG
CAGACCTCTA CCAAGGCCGT GCAGCATTTC TACAACATCA
AACTAGAAGG CAAAGTCCCA ATGCACAAAC TTTTTTTGGA
AATGTTGGAG GCCAAGGTCT GACTAAAAGC TCCCTGGGCC
TTCCCATCCT TCATGTTGAA AAAGGGAAAA TAAACCCAAG
AGTGATGTCG AAGAAACTTA GAGTTTAGTT AACAACATCA
AAAATCAACA GACTGCACTG ATAATTTAGC AGCAAGACTA
TGAAGCAGCT TTCAGATTCC TCCATAGGTT CCTGATGAGT
TCTTTCTACT TTCTCCATCA TCTTCTTTCC TCTTTCTTCC
CACATTTCTC TTTCTCTTTA TTTTTTCTCC TTTTTCTTCTT
TCACCTCCCT TATTTCTTTG CTTCTTTCAT TCCTAGTTCC
CATTCTCCTT TATTTTCTTC CCGTCTGCCT GCCTTCTTTC
TTTTCTTTAC CTACTCTCAT TCCTCTCTTT TCTCATCCTT
CCCCTTTTTT CTAAATTTGA AATAGCTTTA GTTTAAAAAA
AAAAATCCTC CCTTCCCCCT TTCCTTTCCC TTTCTTTCCT
TTTTCCCTTT CCTTTTCCCT TTCCTTTCCT TTCCTCTTGA
CCTTCTTTCC ATCTTTCTTT TTCTTCCTTC TGCTGCTGAA
CTTTTAAAAG AGGTCTCTAA CTGAAGAGAG ATGGAAGCCA
GCCCTGCCAA AGGATGGAGA TCCATAATAT GGATGCCAGT
GAACTTATTG TGAACCATAC CGTCCCCAAT GACTAAGGAA
TCAAAGAGAG AGAACCAACG TTCCTAAAAG TACAGTGCAA
CATATACAAA TTGACTGAGT GCAGTATTAG ATTTCATGGG
AGCAGCCTCT AATTAGACAA CTTAAGCAAC GTTGCATCGG
CTGCTTCTTA TCATTGCTTT TCCATCTAGA TCAGTTACAG
CCATTTGATT CCTTAATTGT TTTTTCAAGT CTTCCAGGTA
TTTGTTAGTT TAGCTACTAT GTAACTTTTT CAGGGAATAG
TTTAAGCTTT ATTCATTCAT GCAATACTAA AGAGAAATAA
GAATACTGCA ATTTTGTGCT GGCTTTGAAC AATTACGAAC
AATAATGAAG GACAAATGAA TCCTGAAGGA AGATTTTTAA
AAATGTTTTG TTTCTTCTTA CAAATGGAGA TTTTTTTGTA
CCAGCTTTAC CACTTTTCAG CCATTTATTA ATATGGGAAT
TTAACTTACT CAAGCAATAG TTGAAGGGAA GGTGCATATT
ATCACGGATG CAATTTATGT TGTGTGCCAG TCTGGTCCCA
AACATCAATT TCTTAACATG AGCTCCAGTT TACCTAAATG
TTCACTGACA CAAAGGATGA GATTACACCT ACAGTGACTC
TGAGTAGTCA CATATATAAG CACTGCACAT GAGATATAGA
TCCGTAGAAT TGTCAGGAGT GCACCTCTCT ACTTGGGAGG
TACAATTGCC ATATGATTTC TAGCTGCCAT GGTGGTTAGG
AATGTGATAC TGCCTGTTTG CAAAGTCACA GACCTTGCCT
CAGAAGGAGC TGTGAGCCAG TATTCATTTA AGAGAATTCC
ACCACACTGG CGGCCCGCGC TTGAT.
```

The present invention also relates to an isolated and purified DNA molecule which encodes a truncated version of nNR2 referred to as nNR2-1. This cDNA molecule is set forth in SEQ ID NO:5 and is disclosed as follows:

(SEQ ID NO:5)
```
GCGGGCCGCC AGTGTGGTGG AATTCGGCTT GTCACTAGGA
GAACATTTGT GTTAATTGCA CTGTGCTCTG TCAAGGAAAC
TTTGATTTAT AGCTGGGGTG CACAAATAAT GGTTGCCGGT
CGCACATGGA TTCGGTAGAA CTTTGCCTTC CTGAATCTTT
TTCCCTGCAC TACGAGGAAG AGCTTCTCTG CAGAATGTCA
AACAAAGATC GACACATTGA TTCCAGCTGT TCGTCCTTCA
TCAAGACGGA ACCTTCCAGC CCAGCCTCCC TGACGGACAG
CGTCAACCAC CACAGCCCTG GTGGCTCTTC AGACGCCAGT
GGGAGCTACA GTTCAACCAT GAATGGCCAT CAGAACGGAC
TTGACTCGCC ACCTCTCTAC CCTTCTGCTC CTATCCTGGG
AGGTAGTGGG CCTGTCAGGA AACTGTATGA TGACTGCTCC
AGCACCATTG TTGAAGATCC CCAGACCAAG TGTGAATACA
```

-continued

```
TGCTCAACTC GATGCCCAAG AGACTGTGTT TAGTGTGTGG
TGACATCGCT TCTGGGTACC ACTATGGGGT AGCATCATGT
GAAGCCTGCA AGGCATTCTT CAAGAGGACA ATTCAAGGCA
ATATAGAATA CAGCTGCCCT GCCACGAATG AATGTGAAAT
CACAAAGCGC AGACGTAAAT CCTGCCAGGC TTGCCGCTTC
ATGAAGTGTT TAAAAGTGGG CATGCTGAAA GAAGGGGTGC
GTCTTGACAG AGTACGTGGA GGTCGGCAGA AGTACAAGCG
CAGGATAGAT GCGGAGAACA GCCCATACCT GAACCCTCAG
CTGGTTCAGC CAGCCAAAAA GCCATATAAC AAGATTGTCT
CACATTTGTT GGTGGCTGAA CCGGAGAAGA TCTATGCCAT
GCCTGACCCT ACTGTCCCCG ACAGTGACAT CAAAGCCCTC
ACTACACTGT GTGACTTGGC CGACCGAGAG TTGGTGGTTA
TCATTGGATG GGCGAAGCAT ATTCCAGGCT TCTCCACGCT
GTCCCTGGCG GACCAGATGA GCCTTCTGCA GAGTGCTTGG
ATGGAAATTT TGATCCTTGG TGTCGTATAC CGGTCTCTTT
CATTTGAGGA TGAACTTGTC TATGCAGACG ATTATATAAT
GGACGAAGAC CAGTCCAAAT TAGCAGGCCT TCTTGATCTA
AATAATGCTA TCCTGCAGCT GGTAAAGAAA TACAAGAGCA
TGAAGCTGGA AAAAGAAGAA TTTGTCACCC TCAAAGCTAT
AGCTCTTGCT AATTCAGACT CCATGCACAT AGAAGATGTT
GAAGCCGTTC AGAAGCTTCA GGATGTCTTA CATGAAGCGC
TGCAGGATTA TGAAGCTGGC CAGCACATGG AGAAGACCCT
CGTCGAGCTG GCAAGATGCT GATGACACTG CCACTCCTGA
GGCAGACCTC TACCAAGGCC GTGCAGCATT TCTACAACAT
CAAACTAGAA GGCAAAGTCC AATGCACAA ACTTTTTTTG
GAAATGTTGG AGGCCAAGGT CTGACTAAAA GCTCCCTGGG
CCTTCCCATC CTTCATGTTG AAAAAGGGAA AATAAACCCA
AGAGTGATGT CGAAGAAACT TAGAGTTTAG TTAACAACAT
CAAAAATCAA CAGACTGCAC TGATAATTTA GCAGCAAGAC
TATGAAGCAG CTTTCAGATT CCTCCATAGG TTCCTGATGA
GTTCTTTCTA CTTTCTCCAT CATCTTCTTT CCTCTTTCTT
CCCACATTTC TCTTTCTCTT TATTTTTTCT CCTTTTCTTC
TTTCACCTCC CTTATTTCTT TGCTTCTTTC ATTCCTAGTT
CCCATTCTCC TTTATTTTCT TCCCGTCTGC CTGCCTTCTT
TCTTTTCTTT ACCTACTCTC ATTCCTCTCT TTTCTCATCC
TTCCCCTTTT TTCTAAATTT GAAATAGCTT TAGTTTAAAA
AAAAAAATCC TCCCTTCCCC CTTTCCTTTC CCTTTCTTTC
CTTTTTCCCT TTCCTTTTCC CTTTCCTTTC CTTTCCTCTT
GACCTTCTTT CCATCTTTCT TTTTCTTCCT TCTGCTGCTG
AACTTTTAAA AGAGGTCTCT AACTGAAGAG AGATGGAAGC
```

-continued

```
CAGCCCTGCC AAAGGATGGA GATCCATAAT ATGGATGCCA
GTGAACTTAT TGTGAACCAT ACCGTCCCCA ATGACTAAGG
AATCAAAGAG AGAGAACCAA CGTTCCTAAA AGTACAGTGC
AACATATACA AATTGACTGA GTGCAGTATT AGATTTCATG
GGAGCAGCCT CTAATTAGAC AACTTAAGCA ACGTTGCATC
GGCTGCTTCT TATCATTGCT TTTCCATCTA GATCAGTTAC
AGCCATTTGA TTCCTTAATT GTTTTTTCAA GTCTTCCAGG
TATTTCTTAG TTTAGCTACT ATGTAACTTT TTCAGGGAAT
AGTTTAAGCT TTATTCATTC ATGCAATACT AAAGAGAAAT
AAGAATACTG CAATTTTGTG CTGGCTTTGA ACAATTACGA
ACAATAATGA AGGACAAATG AATCCTGAAG GAAGATTTTT
AAAAATGTTT TGTTTCTTCT TACAAATGGA GATTTTTTTG
TACCAGCTTT ACCACTTTTC AGCCATTTAT TAATATGGGA
ATTTAACTTA CTCAAGCAAT AGTTGAAGGG AAGGTGCATA
TTATCACGGA TGCAATTTAT GTTGTGTGCC AGTCTGGTCC
CAAACATCAA TTTCTTAACA TGAGCTCCAG TTTACCTAAA
TGTTCACTGA CACAAAGGAT GAGATTACAC CTACAGTGAC
TCTGAGTAGT CACATATATA AGCACTGCAC ATGAGATATA
GATCCGTAGA ATTGTCAGGA GTGCACCTCT CTACTTGGGA
GGTACAATTG CCATATGATT TCTAGCTGCC ATGGTGGTTA
GGAATGTGAT ACTGCCTGTT TGCAAAGTCA CAGACCTTGC
CTCAGAAGGA GCTGTGAGCC AGTATTCATT TAAGAGAATT
CCACCACACT GGCGGCCCGC GCTTGAT
```

The present invention also relates to a substantially purified form of the novel nuclear trans-acting receptor protein, nNR1, which is shown in FIGS. 2A–F and FIG. 3 and as set forth in SEQ ID NO:2, disclosed as follows:

```
                                          (SEQ ID NO:2)
MSSDDRHLGS SCGSFIKTEP SSPSSGIDAL SHHSPSGSSD

ASGGFGLALG THANGLDSPP MFAGAGLGGT PCRKSYEDCA

SGIMEDSAIK CEYMLNAIPK RLCLVCGDIA SGYHYGVASC

EACKAFFKRT IQGNIEYSCP ATNECEITKR RRKSCQACRF

MKCLKVGMLK EGVRLDRVRG GRQKYKRRLD SESSPYLSLQ

ISPPAKKPLT KIVSYLLVAE PDKLYAMPPP GMPEGDIKAL

TTLCDLADRE LVVIIGWAKH IPGFSSLSLG DQMSLLQSAW

MEILILGIVY RSLPYDDKLV YAEDYIMDEE HSRLAGLLEL

YRAILQLVRR YKKLKVEKEE FVTLKAAALA NSDSMYIEDL

EAVQKLQDLL HEALQDYELS QRHEEPWRTG KLLLTLPLLR

QTAAKAVQHF YSVKLQGKVP MHKLFLEMLE AKAWARADSL

QEWRPLEQVP SPLHRATKRQ HVHFLTPLPP PPSVAWVGTA

QAGYHLEVFL PQRAGWPRAA
```

The present invention also relates to biologically active fragments and/or mutants of nNR1 as set forth as SEQ ID NO:2, including but not necessarily limited to amino acid substitutions, deletions, additions, amino terminal truncations and carboxy-terminal truncations such that these mutations provide for proteins or protein fragments of diagnostic, therapuetic or prophylatic use and would be useful for screening for agonists and/or antaganists of nNR1 function.

The present invention also relates to a substantially purified form of the novel nuclear trans-acting receptor protein, nNR2, which is shown in FIGS. 5A–E and FIG. 6 and as set forth in SEQ ID NO:4, disclosed as follows:

```
                                           (SEQ ID NO:4)
MDSVELCLPE SFSLHYEEEL LCRMSNKDRH IDSSCSSFIK

TEPSSPASLT DSVNHHSPGG SSDASGSYSS TMNGHQNGLD

SPPLYPSAPI LGGSGPVRKL YDDCSSTIVE DPQTKCEYML

NSMPKRLCLV CGDIASGYHY GVASCEACKA FFKRTIQGNI

EYSCPATNEC EITKRRRKSC QACRFMKCLK VGMLKEGVRL

DRVRGGRQKY KRRIDAENSP YLNPQLVQPA KKPYNKIVSH

LLVAEPEKIY AMPDPTVPDS DIKALTTLCD LADRELVVII

GWAKHIPGFS TLSLADQMSL LQSAWMEILI LGVVYRSLSF

EDELVYADDY IMDEDQSKLA GLLDLNNAIL QLVKKYKSMK

LEKEEFVTLK AIALANSDSM HIEDVEAVQK LQDVLHEALQ

DYEAGQHMED PRRAGKMLMT LPLLRQTSTK AVQHFYNIKL

EGKVPMHKLF LEMLEAKV.
```

The present invention also relates to biligically active fragments and/or mutants of nNR2 as set forth as SEQ ID NO:4, including but not necessarily limited to amino acid substitutions, deletions, additions, amino terminal truncations and carboxy-terminal truncations such that these mutations provide for proteins or protein fragments of diagnostic, therepuetic or prophylactic use and would be useful for screening for agonists and/or antagonists of nNR2 function. To this end, an example of such a protein is the carboxy-terminal truncated version of nNR2, referred to as nNR2-1 and described in FIG. 8 and set forth as SEQ ID NO:6, as follows:

```
                                           (SEQ ID NO:6)
MDSVELCLPE SFSLHYEEEL LCRMSNKDRH IDSSCSSFIK

TEPSSPASLT DSVNHHSPCG SSDASGSYSS TMNCHQNGLD

SPPLYPSAPI LGGSGPVRKL YDDCSSTIVE DPQTKCEYML

NSMPKRLCLV CGDIASGYHY GVASCEACKA FFKRTIQGNI

EYSCPATNEC EITKRRRKSC QACRFMKCLK VGMLKEGVRL

DRVRGGRQKY KRRIDAENSP YLNPQLVQPA KKPYNKIVSH

LLVAEPEKIY AMPDPTVPDS DIKALTTLCD LADRELVVII

GWAKHIPGFS TLSLADQMSL LQSAWMEILI LGVVYRSLSF

EDELVYADDY IMDEDQSKLA GLLDLNNAIL QLVKKYKSMK

LEKEEFVTLK AIALANSDSM HIEDVEAVQK LQDVLHEALQ
```

-continued

```
DYEAGQHMEK TLVELARC.
```

The present invention also relates to isolated nucleic acid molecules which are fusion constructions expressing fusion proteins useful in assays to identify compounds which modulate wild-type human nNR1, nNR2 and/or nNR2-1 activity. A preferred aspect of this portion of the invention includes, but is not limited to, glutathione S-transferase GST-nNR1 and/or GST-nNR2 fusion constructs. These fusion constructs include, but are not limited to, all or a portion of the ligand-binding domain of nNR1, nNR2 and/or nNR2-1, respectively, as an in-frame fusion at the carboxy terminus of the GST gene. The disclosure of SEQ ID NOS:1–4 allow the artisan of ordinary skill to construct any such nucleic acid molecule encoding a GST-nuclear receptor fusion protein. Soluble recombinant GST-nuclear receptor fusion proteins may be expressed in various expression systems, including *Spodoptera frugiperda* (Sf21) insect cells (Invitrogen) using a baculovirus expression vector (e.g., Bac-N-Blue DNA from Invitrogen or pAcG2T from Pharmingen).

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

It is known that there is a substantial amount of redundancy in the various codons which code for specific amino acids. Therefore, this invention is also directed to those DNA sequences encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UU
G=Gly=Glycine: codons GGA, GGC, GGG, GGU
H=His=Histidine: codons CAC, CAU
I=Ile=Isoleucine: codons AUA, AUC, AWU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinty of an enzyme for a substrate or a receptor for a ligand.

As used herein, "purified" and "isolated" are utilized interchangeably to stand for the proposition that the nucleic acid, protein, or respective fragment thereof in question has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in pure quantities so as to afford the opportunity to generate polyclonal antibodies, monoclonal antibodies, amino acid sequencing, and peptide digestion. Therefore, the nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods while a chemically synthesized nucleic acid sequence is considered to be substantially purified when purified from its chemical precursors.

The present invention also relates to recombinant vectors and recombinant hosts, both prokaryotic and eukaryotic, which contain the substantially purified nucleic acid molecules disclosed throughout this specification.

Therefore, the present invention also relates to methods of expressing nNR1, nNR2 and/or nNR2-1 and biological equivalents disclosed herein, assays employing these recombinantly expressed gene products, cells expressing these gene products, and agonistic and/or antagonistic compounds identified through the use of assays utilizing these recombinant forms, including, but not limited to, one or more modulators of the human nNR1, nNR2 and/or nNR2-1 either through direct contact LBD or through direct or indirect contact with a ligand which either interacts with the DBD or with the wild-type transcription complex which either nNR1, nNR2 and/or nNR2-1 interacts in trans, thereby modulating cell differentiation or cell development.

As used herein, a "biologically active equivalent" or "functional derivative" of a wild-type human nNR1, nNR2 and/or nNR2-1 possesses a biological activity that is substantially similar to the biological activity of the wild type human nNR1, nNR2 and/or nNR2-1. The term "functional derivative" is intended to include the "fragments," "mutants," "variants," "degenerate variants," "analogs" and "homologues" or to "chemical derivatives" of the wild type human nNR1, nNR2 and/or nNR2-1 protein. The term "fragment" is meant to refer to any polypeptide subset of wild-type human nNR1 or nNR2. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the human nNR1, nNR2 and/or nNR2-1 or human nNR1, nNR2 and/or nNR2-1 functional derivatives. The term "variant" is meant to refer to a molecule substantially similar in structure and function to either the entire wild-type protein or to a fragment thereof. A molecule is "substantially similar" to a wild-type human nNR1, nNR2 and/or nNR2-1-like protein if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the full-length human nNR1, nNR2 and/or nNR2-1 protein or to a biologically active fragment thereof.

Any of a variety of procedures may be used to clone human nNR1, nNR2 and/or nNR2-1. These methods include, but are not limited to, (1) a RACE PCR cloning technique (Frohman, et al., 1988, *Proc. Natl. Acad. Sci. USA* 85: 8998–9002). 5' and/or 3' RACE may be performed to generate a full-length cDNA sequence. This strategy involves using gene-specific oligonucleotide primers for PCR amplification of human nNR1, nNR2 and/or nNR2-1 cDNA. These gene-specific primers are designed through identification of an expressed sequence tag (EST) nucleotide sequence which has been identified by searching any number of publicly available nucleic acid and protein databases; (2) direct functional expression of the human nNR1, nNR2 and/or nNR2-1 cDNA following the construction of a human nNR1, nNR2 and/or nNR2-1-containing cDNA library in an appropriate expression vector system; (3) screening a human nNR1, nNR2 and/or nNR2-1-containing cDNA library constructed in a bacteriophage or plasmid shuttle vector with a labeled degenerate oligonucleotide probe designed from the amino acid sequence of the human nNR1, nNR2 and/or nNR2-1 protein; (4) screening a human nNR1, nNR2 and/or nNR2-1-containing cDNA library constructed in a bacteriophage or plasmid shuttle vector with a partial cDNA encoding the human nNR1, nNR2 and/or nNR2-1 protein. This partial cDNA is obtained by the specific PCR amplification of human nNR1, nNR2 and/or nNR2-1 DNA fragments through the design of degenerate oligonucleotide primers from the amino acid sequence known for other kinases which are related to the human nNR1, nNR2 and/or nNR2-1 protein; (5) screening a human nNR1, nNR2 and/or nNR2-1-containing cDNA library constructed in a bacteriophage or plasmid shuttle vector with a partial cDNA encoding the human nNR1, nNR2 and/or nNR2-1 protein. This strategy may also involve using gene-specific oligonucleotide primers for PCR amplification of human nNR1, nNR2 and/or nNR2-1 cDNA identified as an EST as described above; or (6) designing 5' and 3' gene specific oligonucleotides using SEQ ID NO: 1 as a template so that either the full-length cDNA may be generated by known PCR techniques, or a portion of the coding region may be generated by these same known PCR techniques to generate and isolate a portion of the coding region to use as a probe to screen one of numerous types of cDNA and/or genomic libraries in order to isolate a full-length version of the nucleotide sequence encoding human nNR1, nNR2 and/or nNR2-1.

It is readily apparent to those skilled in the art that other types of libraries, as well as libraries constructed from other cell types-or species types, may be useful for isolating a nNR1, nNR2 and/or nNR2-1-encoding DNA or a nNR1, nNR2 and/or nNR2-1 homologue. Other types of libraries include, but are not limited to, cDNA libraries derived from other cells or cell lines other than human cells or tissue such as murine cells, rodent cells or any other such vertebrate host which may contain nNR1, nNR2 and/or nNR2-1-encoding DNA. Additionally a nNR1, nNR2 and/or nNR2-1 gene and homologues may be isolated by oligonucleotide- or polynucleotide-based hybridization screening of a vertebrate genomic library, including but not limited to, a murine genomic library, a rodent genomic library, as well as concomitant human genomic DNA libraries.

It is readily apparent to those skilled in the art that suitable cDNA libraries may be prepared from cells or cell lines which have nNR1, nNR2 and/or nNR2-1 activity. The selection of cells or cell lines for use in preparing a cDNA library to isolate a cDNA encoding nNR1, nNR2 and/or nNR2-1 may be done by first measuring cell-associated nNR1, nNR2 and/or nNR2-1 activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding human nNR1, nNR2 and/or nNR2-1 may also be isolated from a suitable genomic DNA library. Construction of genomic DNA libraries can be performed by standard techniques well known in the art. Well known genomic DNA library construction techniques can be found in Sambrook, et al., supra.

In order to clone the human nNR1, nNR2 and/or nNR2-1 gene by one of the preferred methods, the amino add sequence or DNA sequence of human nNR1, nNR2 and/or nNR2-1 or a homologous protein may be necessary. To accomplish this, the nNR1, nNR2 and/or nNR2-1 protein or a homologous protein may be purified and partial amino acid sequence determined by automated sequnators. It is not necessary to determine the entire amino acid sequence, but the linear sequence of two regions of 6 to 8 amino acids can be determined for the PCR amplification of a partial human nNR1, nNR2 and/or nNR2-1 DNA fragment. Once suitable amino add sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the human nNR1, nNR2 and/or nNR2-1 sequence but others in the set will be capable of hybridizing to human nNR1, nNR2 and/or nNR2-1 DNA even in the presence of DNA oligonucleotides with mismatches. The mismatched DNA oligonucleotides may still sufficiently hybridize to the human nNR1, nNR2 and/or nNR2-1 DNA to permit identification and isolation of human nNR1, nNR2 and/or nNR2-1 encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO: 1, either for the purpose of isolating overlapping 5' and 3' RACE products for generation of a full-length sequence coding for human nNR1, nNR2 and/or nNR2-1, or to isolate a portion of the nucleotide sequence coding for human nNR1, nNR2 and/or nNR2-1 for use as a probe to screen one or more cDNA- or genomic-based libraries to isolate a fill-length sequence encoding human nNR1, nNR2 and/or nNR2-1 or human nNR1, nNR2 and/or nNR2-1-like proteins.

In an exemplified method, the human nNR1, nNR2 and/or nNR2-1 full-length cDNA of the present invention were generated by PCR scanning human cDNA libraries with oligonucleotide primers generated from ESTs showing homology to hERR2. Briefly, random and oligo dT primed cDNA libraries as described herein which consist of approximately 4 million primary clones were constructed in the plasmid vector pBluescript (Stratagene, LaJolla, Calif.). The primary clones were subdivided into 188 pools with each pool containing ~20,000 clones. Each pool was amplified separately and the resulting plasmid pools were collected and transferred into two 96-well plates. Primer pairs from the 5' and 3' portion of an EST are used to scan the respective cDNA library distributed in a 96-well plate. Initial positive pools are identified with EST primers. Corresponding fill length cDNA clones were retrieved via inverse PCR using primer pairs designed from the EST which are back to back against each other. Therefore, the primers walk away from each other during the PCR reaction, resulting in amplification of a population of linearized plasmid DNA molecules corresponding to the EST. cDNA clones were obtained by ligating linear DNA and transforming the circularized DNA into bacteria competent cells. Usually, four positive clones for each gene were used for sequence analysis because of the possibility of mutation during long PCR reactions. The consensus DNA sequence is considered as the wild type DNA sequence. Recloning of the gene through PCR using gene specific primers covering the whole open reading frame was done so as to obtain a cDNA clone which has an identical DNA sequence to the consensus sequence. This procedure does not depend upon using a cDNA library with directionally cloned inserts, but does require cDNA libraries constructed in a plasmid vector, such as pBluescript. This procedure was utilized to identify fill length cDNA molecules representing human nNR1, nNR2 and/or nNR2-1.

A variety of mammalian expression vectors may be used to express recombinant human nNR1, nNR2 and/or nNR2-1 in mammalian cells. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

Commercially available mammalian expression vectors which may be suitable for recombinant human nNR1, nNR2 and/or nNR2-1 expression, include but are not limited to, pcDNA3.1 (Invitrogen), pLITMUS28, pLITMUS29, pLITMUS38 and pLITMUS39 (New England Bioloabs), pcDNAI, pcDNAIamp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MM eo(342-12) (ATCC 37224), pRSVgpt (ATCC 37199), pRSVneo (ATCC 37198), pSV2-dhfr (ATCC 37146), pUCTag (ATCC 37460), and lZD35 (ATCC 37565).

A variety of bacterial expression vectors may be used to express recombinant human nNR1, nNR2 and/or nNR2-1 in bacterial cells. Commercially available bacterial expression vectors which may be suitable for recombinant human nNR1, nNR2 and/or nNR2-1 expression include, but are not limited to pQE (Qiagen), pET11a (Novagen), lambda gt11 (Invitrogen), and pKK223-3 (Pharmacia).

A variety of fungal cell expression vectors may be used to express recombinant human nNR1, nNR2 and/or nNR2-1 in fungal cells. Commercially available fugal cell expression vectors which may be suitable for recombinant human nNR1, nNR2 and/or nNR2-1 expression include but are not limited to pYES2 (invitrogen) and Pichia expression vector (Invitrogen).

A variety of insect cell expression vectors may be used to express recombinant receptor in insect cells. Commercially available insect cell expression vectors which may be suitable for recombinant expression of human nNR1, nNR2 and/or nNR2-1 include but are not limited to pBlueBacIII and pBlueBacHis2 (Invitrogen), and pAcG2T (Pharmingen).

An expression vector containing DNA encoding a human nNR1, nNR2 and/or nNR2-1-like protein may be used for expression of human nNR1, nNR2 and/or nNR2-1 in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila- and silkworm-derived cell lines. Cell lines derived from mammalian species which may be suitable and which are commercially available, include but are not limited to, L cells L-M(TK–) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209).

The expression vector may be introduced into host cells via any one of a number of techniques including but not limited to transformation, transfection, protoplast fusion, and electroporation. The expression vector-containing cells are individually analyzed to determine whether they produce human nNR1, nNR2 and/or nNR2-1 protein. Identification of human nNR1, nNR2 and/or nNR2-1 expressing cells may be done by several means, including but not limited to immunological reactivity with anti-human nNR1, nNR2 and/or nNR2-1 antibodies, labeled ligand binding and the presence of host cell-associated human nNR1, nNR2 and/or nNR2-1 activity.

The cloned human nNR1, nNR2 and/or nNR2-1 cDNA obtained through the methods described above may be recombinantly expressed by molecular cloning into an expression vector (such as pcDNA3.1, pQE, pBlueBacHis2 and pLITMUS28) containing a suitable promoter and other appropriate transcription regulatory elements, and transferred into prokaryotic or eukaryotic host cells to produce recombinant human nNR1, nNR2 and/or nNR2-1. Techniques for such manipulations can be found described in Sambrook, et al., supra, are discussed at length in the Example section and are well known and easily available to the artisan of ordinary skill in the art.

Expression of human nNR1, nNR2 and/or nNR2-1 DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the human nNR1, nNR2 and/or nNR2-1 cDNA sequence(s) that yields optimal levels of human nNR1, nNR2 and/or nNR2-1, cDNA molecules including but not limited to the following can be constructed: a cDNA fragment containing the full-length open reading frame for human nNR1, nNR2 and/or nNR2-1 as well as various constructs containing portions of the cDNA encoding only specific domains of the protein or rearranged domains of the protein. All constructs can be designed to contain none, all or portions of the 5' and/or 3' untranslated region of a human nNR1, nNR2 and/or nNR2-1 cDNA. The expression levels and activity of human nNR1, nNR2 and/or nNR2-1 can be determined following the introduction, both singly and in combination, of these constructs into appropriate host cells. Following determination of the human nNR1, nNR2 and/or nNR2-1 cDNA cassette yielding optimal expression in transient assays, this nNR1, nNR2 and/or nNR2-1 cDNA construct is transferred to a variety of expression vectors (including recombinant viruses), including but not limited to those for mammalian cells, plant cells, insect cells, oocytes, bacteria, and yeast cells.

The present invention also relates to polyclonal and monoclonal antibodies raised in response to either the human form of nNR1, nNR2 and/or nNR2-1 disclosed herein, or a biologically active fragment thereof. It will be especially preferable to raise antibodies against epitopes within the $NH_2$-terminal domain of nNR1, nNR2 and/or nNR2-1, which show the least homology to other known proteins belonging to the human nuclear receptor superfamily.

Recombinant nNR1, nNR2 and/or nNR2-1 protein can be separated from other cellular proteins by use of an immunoaffinity column made with monoclonal or polyclonal antibodies specific for full-length nNR1, nNR2 and/or nNR2-1 protein, or polypeptide fragments of nNR1, nNR2 and/or nNR2-1 protein. Additionally, polyclonal or monoclonal antibodies may be raised against a synthetic peptide (usually from about 9 to about 25 amino acids in length) from a portion of the protein as disclosed in SEQ ID NO:2. Monospecific antibodies to human nNR1, nNR2 and/or nNR2-1 are purified from mammalian antisera containing antibodies reactive against human nNR1, nNR2 and/or nNR2-1 or are prepared as monoclonal antibodies reactive with human nNR1, nNR2 and/or nNR2-1 using the technique of Kohler and Milstein (1975, *Nature* 256: 495–497). Monospecific antibody as used herein is defined as a single antibody species or multiple antibody species with homogenous binding characteristics for human nNR1, nNR2 and/or nNR2-1. Homogenous binding as used herein refers to the ability of the antibody species to bind to a specific antigen or epitope, such as those associated with human nNR1, nNR2 and/or nNR2-1, as described above. Human nNR1, nNR2 and/or nNR2-1-specific antibodies are raised by immunizing animals such as mice, rats, guinea pigs, rabbits, goats, horses and the like, with an appropriate concentration of human nNR1, nNR2 and/or nNR2-1 protein or a synthetic peptide generated from a portion of human nNR1, nNR2 and/or nNR2-1 with or without an immune adjuvant.

Preimmune serum is collected prior to the first immunization. Each animal receives between about 0.1 mg and about 1000 mg of human nNR1, nNR2 and/or nNR2-1 protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of human nNR1, nNR2 and/or nNR2-1 protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of human nNR1, nNR2 and/or nNR2-1 in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with human nNR1, nNR2 and/or nNR2-1 are prepared by immunizing inbred mice, preferably Balb/c, with human nNR1, nNR2 and/or nNR2-1 protein. The mice are immunized by the IP or SC route with about 1 mg to about 100 mg, preferably about 10 mg, of human nNR1, nNR2 and/or nNR2-1 protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of human nNR1, nNR2 and/or nNR2-1 in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using human nNR1, nNR2 and/or nNR2-1 as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-human nNR1, nNR2 and/or nNR2-1 mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of human nNR1, nNR2 and/or nNR2-1 in body fluids or tissue and cell extracts.

It is readily apparent to those skilled in the art that the above described methods for producing monospecific antibodies may be utilized to produce antibodies specific for human nNR1, nNR2 and/or nNR2-1 peptide fragments, or full-length human nNR1, nNR2 and/or nNR2-1.

Human nNR1, nNR2 and/or nNR2-1 antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing full-length human nNR1, nNR2 and/or nNR2-1 or human nNR1, nNR2 and/or nNR2-1 protein fragments are slowly passed through the column. The column is then washed with phosphate buffered saline until the optical density ($A_{280}$) falls to background, then the protein is eluted with 0.23 M glycine-HCl (pH 2.6). The purified human nNR1, nNR2 and/or nNR2-1 protein is then dialyzed against phosphate buffered saline.

Levels of human nNR1, nNR2 and/or nNR2-1 in host cells is quantified by a variety of techniques including, but not limited to, immunoaffinity and/or ligand affinity techniques. nNR1, nNR2 and/or nNR2-1-specific affinity beads or nNR1, nNR2 and/or nNR2-1-specific antibodies are used to isolate $^{35}$S-methionine labeled or unlabelled nNR1, nNR2 and/or nNR2-1. Labeled nNR1, nNR2 and/or nNR2-1 protein is analyzed by SDS-PAGE. Unlabelled nNR1, nNR2 and/or nNR2-1 protein is detected by Western blotting, ELISA or RIA assays employing either nNR1, nNR2 and/or nNR2-1 protein specific antibodies and/or antiphosphotyrosine antibodies.

Following expression of nNR1, nNR2 and/or nNR2-1 in a host cell, nNR1, nNR2 and/or nNR2-1 protein may be recovered to provide nNR1, nNR2 and/or nNR2-1 protein in active form. Several nNR1, nNR2 and/or nNR2-1 protein purification procedures are available and suitable for use. Recombinant nNR1, nNR2 and/or nNR2-1 protein may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

The present invention is also directed to methods for screening for compounds which modulate the expression of DNA or RNA encoding a human nNNR1, nNR2 and/or nNR2-1 protein. Compounds which modulate these activities may be DNA, RNA, peptides, proteins, or non-proteinaceous organic molecules. Compounds may modulate by increasing or attenuating the expression of DNA or RNA encoding human nNR1, nNR2 and/or nNR2-1, or the function of human nNR1, nNR2 and/or nNR2-1. Compounds that modulate the expression of DNA or RNA encoding human nNR1, nNR2 and/or nNR2-1 or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing human nNR1, nNR2 and/or nNR2-1, antibodies to human nNR1, nNR2 and/or nNR2-1, or modified human nNR1, nNR2 and/or nNR2-1 may be prepared by known methods for such uses.

The DNA molecules, RNA molecules, recombinant protein and antibodies of the present invention may be used to screen and measure levels of human nNR1, nNR2 and/or nNR2-1. The recombinant proteins, DNA molecules, RNA molecules and antibodies lend themselves to the formulation of kits suitable for the detection and typing of human nNR1, nNR2 and/or nNR2-1. Such a kit would comprise a compartmentalized carrier suitable to hold in close confinement at least one container. The carrier would further comprise reagents such as recombinant nNR1, nNR2 and/or nNR2-1 or anti-nNR1, nNR2 and/or nNR2-1 antibodies suitable for detecting human nNR1, nNR2 and/or nNR2-1. The carrier may also contain a means for detection such as labeled antigen or enzyme substrates or the like.

Pharmaceutically useful compositions comprising modulators of human nNR1, nNR2 and/or nNR2-1 may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified human nNR1, nNR2 and/or nNR2-1, or either nNR1, nNR2 and/or nNR2-1 agonists or antagonists.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life; absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are provided to illustrate the present invention without, however, limiting the same hereto.

EXAMPLE 1

Isolation and Characterization of DNA Fragments Encoding nNR1, nNR2 and/or nNR2-1

The DNA sequences from several representative subfamilies (Giguère, et al., 1988, *Nature 331: 91–94*) were used to query the EST database by using the Blastn program. Two ESTs (Genbank accession number h91890 (nNR1) and w26275 (nNR2)) were identified with homology to human ERR2 at DNA sequence level.

EST h91890 is disclosed herein as SEQ ID NO:7 and is as set forth:

(SEQ ID NO:7)
CTTTTTAGGA GGTGGAGAAA TTTGTAAGCT CAGGTATGGG

CTGCTCTCTG AGTCCAGCCG TCGCTTGTAT TTCTGACGGC

CTCCACGCAC TCGATCAAGG CGCACACCTT CCTTCAGCAT

CCCCACTTTG AGGCATTTCA TGAAGCGGCA GGCCTGGCAG

GACTTGCGCC TCCGTTTGGT GATCTCGCAC TCGTTGGTGG

CCGGGCAGCT GTACTCAATG TTCCCTTGGA TAGTCCTCTT

GAAGAAGGCC TTGCAAGCCT CGCAGGAGGC CCACGCGTNA

GTGGTAGCCA GAGNAAATGT CCCCGCACAC GAGGCACAGG

CGCTTGGGGA TGGCGTTGAG CATGTTACTT CGCACTTGGA

TGGGCCGAGT CCTCCATGGA TGGCCGCTGG CAACAGTTCC

TCG.

EST w26275 is disclosed herein as SEQ ID NO:8 and is as set forth:

(SEQ ID NO:8)
CNNNNNNNNN NNNTTTTNNT GCCTAAAGTG GTACCCNGAA

GNGATGTCAC CACACACTAA ACACAGTCTC TTGGGCATCG

AGTTGAGCAT GTATTCACAC TTGGTCTGGG GATCTTCAAC

AATGGTGCTG GAGCAGTCAT CATACAGTTT CCTGACAGGC

CCACTACCTC CCAGGATAGG AGCAGAAGGG TAGAGAGGTG

GCGAGTCAAG TCCGTTCTGA TGGCCATTCA TGGTTGAACT

GTAGCTCCCA CTGGCGTCTG AAGAGCCACC AGGGCTGTGG

TGGTTGACGC TGTCCGTCAG GGAGGCTGGG CTGGAAGGTT

CCGTCTTGAT GAAGGACGAA CAGCTGGAAT CAATGTGTCG

ATCTTTGTTT GGACATTCTG CAGAGAAGCT CTTCCTCCGT

NGTGCAGGGA AAAAGATTCA GGAAGGCAAA GTTCTTCCCG

AATCCATGTG CGACCGGAAA CCATTATTTG NGCACCCCAG

CTATTAATCA AAGTTCCTTG ACAGAGACAG GGCAATTACA

NAATGTCTCC TNTNGGGGAT CAACTGTTCN GTATTNNNNN

NNNNNNNNNN NNNNNNNNNN NNNNNNNNNN NNNNNNNNNN

NNNNNNNNNN NNNNNNNNNN TT.

Primer pairs 5'-TGAGTCCAGCCGTCGCTTGTAT-3' (ERR4F1; SEQ ID NO:9), 5'-TGCAAGCCTCGCAGGAGGCC-3' (ERR4iF1; SEQ ID NO:10), and 5'-GGCCTTCTTCAAGAGGACTATC-3' (ERR4R1; SEQ ID NO:11) were designed from h91890; 5'-AAAGATCGACACATTGATTCC-3' (ERR5F; SEQ ID NO:12), 5'-GACTTGACTCGCCACCTCTC-3' (ERR5iF; SEQ ID NO:13) and 5'-GTTCTGATGGCCATTCATGGT-3' (ERR5R; SEQ ID NO:14) were designed from W26275. Primer pairs ERR4F/ERR4R and ERR5F/ERR5R were used to scan cDNA made from testis, fetal brain, prostate and placenta first before scaning cDNA libraries made from those cDNA and distributed in 96-well plates. Primers for nNR1 produced a PCR product from testis cDNA, while primers for nNR2 generated a PCR product a cDNA library generated from fetal brain, prostate and placenta mRNA. Therefore, a cDNA library made from testis with >2.5 kb insert was used for nNR1 positive pool identification, and A4 and G8 gave the PCR product of expected size. Inverse PCR using ERR4iF1 and ERR4R1 were performed on positive pools and DNA fragments of about 6.0 kb were amplified. The DNA fragment was purified using Qiagen gel extraction kit. Phosphorylation, self-ligation and transformation of the purified DNA was carried out. DNA minipreps from four individual clones were used in automated sequencing with gene specific and vector primers. Since a PCR-induced mutation is possible in long PCR reactions, nNR1 was re-subcloned in to the PCR2.1 vector (Invitrogen) using a PCR fragment amplified by a 5'-primer 5'-GAATATGATGACCCTAATGCA-3' (SEQ ID NO:15) and a 3'-primer 5'-CTTCCACCTCATGGACACCAA-3' (SEQ ID NO:16) on the positive A4 pool. One out of the four TA-clones showed no mutation through sequencing confirmation. DNA sequence analysis was performed using the ABI PRISM™ dye terminator cycle sequencing ready reaction kit with AmpliTaq DNA polymerase, FS (Perkin Elmer, Norwalk, Conn.). DNA sequence analysis was performed with M13 forward/reverse primers and gene specific sequencing primers manufactured by GIBCO BRL (Gaithersburg, Md.). Sequence assembly and analysis were performed with SEQUENCHER™ 3.0 (Gene Codes Corporation, Ann Arbor, Mich.). Ambiguities and/or discrepancies between automated base calling in sequencing reads were visually examined and edited to the correct base call. Several regions were resequenced after initial automated or visual calling. Four oligonucleotides close to the regions with potential sequence ambiguities were utilized ([R1F1] 5'-CAT TCC ACG GAG GCA TCC TC-3' (SEQ ID NO:23); [R1F2] 5'-CCA AGG CCG TGC AGC ACT TC-3' (SEQ ID NO:24); [R1R1] 5'-GAC AGC CTC TAG ATC CTC GAT-3' (SEQ ID NO:25); and, [R1R2] 5'-ATC ATG GCT TGA CAT TCT TTC-3' (SEQ ID NO:26) and automated sequencing was performed. The final nucleotide sequence encoding NR1 is shown as set forth in FIGS. 1A–C and as set forth as SEQ ID NO:1

For nNR2, a cDNA library made from fetal brain with >2.5 kb insert was used. Positive pools C1, F7 and G6 were identified and used in inverse PCR with primer pairs ERR5iF/ERR5R. A PCR fragment of ~6.0 kb was amplified from C1. The same methodology as described herein for nNR1 was applied to isolation, characterization and sequencing of a nNR2 cDNA. The cDNA fragment cloned into pCR2.1 vector was amplified by 5'-primer 5'-GTTAATTGCACTGTGCTCTG-3' (SEQ ID NO:17) and 3'-primer 5'-AGTGTGGTGGAATTCTCTTA-3' (SEQ ID NO:18).

Primer pairs XR2F3 (5'-AGCTCTTGCTAATTCAGAC-3' [SEQ ID NO:27]) and XR2R4 (5'-TCAACATGAAGGATGGGAAGG-3' [SEQ ID NO:28]) were used in DNA sequence analysis (performed using the ABI PRISM™ dye terminator cycle sequencing ready reaction kit with AmpliTaq DNA polymerase, FS (Perkin Elmer, Norwalk, Conn.)) of the carboxy region of nNR2. DNA sequence analysis was performed with M13 forward/reverse primers and gene specific sequencing primers customarily manufactured by GIBCO BRL (Gaithersburg, Md.). Sequence assembly and analysis were performed with SEQUENCHER™ 3.0 (Gene Codes Corporation, Ann Arbor, Mich.). Ambiguities and/or discrepancies between automated base calling in sequencing reads were visually examined and edited to the correct base call. Resequencing of the ligand binding domain showed a new open reading frame that was confirmed with the XR2F3/ XR2R4 primers. The nNR2 peptide coded by the complete open reading frame has 40 extra amino acids at C-terminus compared to nNR2-1 and is similar in length to its closest related member hERR2.

In order to identify the genome map position of the genes, primers in the 3' non-coding region were designed. Forwarding primer 5'-TCTAGTGTTGCTGCGAGTGAC-3' (SEQ ID NO:19) and reversing primer 5'-CTTCCACCTCATGGACACCAA-3' (SEQ ID NO:20) were used for nNR1, while forwarding primer 5'-GTCTGACTAAAAGCTCCCTG-3' (SEQ ID NO:21) and reversing primer 5'-GAAGATGATGGAGAAAGTAGA-3' (SEQ ID NO:22) were used for nNR2. PCR scanning was performed on the 83 clones of the Stanford radiation hybrid panel (Cox et al., 1990, Science, 250:245:250). The PCR results were scored and submitted to the Stanford Genome Center for linkage analysis. The results indicate that nNR1 is located on locus 14q24.3~14q31 and nNR2 is located on chromosome 1.

SEQUENCE LISTING

<160> NUMBER OF SEQ ID NOS: 30

<210> SEQ ID NO 1
<211> LENGTH: 2807
<212> TYPE: DNA
<213> ORGANISM: Human

<400> SEQUENCE: 1

```
gaatatgatg accctaatgc aacaatatct aacatactat ccgagcttcg gtcatttgga      60
agaactgcag attttcctcc ttcaaaatta aagtcaggtt atggagaaca tgtatgctat     120
gttcttgatt gcttcgctga agaagcattg aaatatattg gtttcacctg gaaaaggcca     180
atatacccag tagaagaatt agaagaagaa agcgttgcag aagatgatgc agaattaaca     240
ttaaataaag tggatgaaga atttgtggaa gaagagacag ataatgaaga aaactttatt     300
gatctcaacg ttttaaaggc ccagacatat cacttggata tgaacgagac tgccaaacaa     360
gaagatattt tggaatccac aacagatgct gcagaatgga gcctagaagt ggaacgtgta     420
ctaccgcaac tgaaagtcac gattaggact gacaataagg attggagaat ccatgttgac     480
caaatgcacc agcacagaag tggaattgaa tctgctctaa aggagaccaa gggattttg      540
gacaaactcc ataatgaaat tactaggact ttggaaaaga tcagcagccg agaaaagtac     600
atcaacaatc agccgggagc ccatggagca ctgtcctcag agatgcgcag gttaggctca     660
ctgtctaggc caggcccacc ttagtcactg tggactggca atggaagctc ttcctggaca     720
cacctgccct agccctcacc ctggggtgga agagaaatga gcttggcttg caactcagac     780
cattccacgg aggcatcctc cccttccctg ggctggtgaa taaagtttc ctgaggtcaa      840
ggacttcctt ttccctgcca aaatggtgtc cagaactttg aggccagagg tgatccagtg     900
atttgggagc tgcaggtcac acaggctgct cagagggctg ctgaacagga tgtcctcgga     960
cgacaggcac ctgggctcca gctgcggctc cttcatcaag actgagccgt ccagcccgtc    1020
ctcgggcata gatgccctca gccaccacag ccccagtggc tcgtccgacg ccagcggcgg    1080
ctttggcctg gccctgggca cccacgccaa cggtctggac tcgccaccca tgtttgcagg    1140
cgccgggctg ggaggcaccc catgccgcaa gagctacgag gactgtgcca gcggcatcat    1200
ggaggactcg gccatcaagt gcgagtacat gctcaacgcc atccccaagc gcctgtgcct    1260
cgtgtgcggg gacattgcct ctggctacca ctacggcgtg gcctcctgcg aggcttgcaa    1320
ggccttcttc aagaggacta tccaagggaa cattgagtac agctgcccgg ccaccaacga    1380
gtgcgagatc accaaacgga ggcgcaagtc ctgccaggcc tgccgcttca tgaaatgcct    1440
caaagtgggg atgctgaagg aaggtgtgcg ccttgatcga gtgcgtggag gccgtcagaa    1500
atacaagcga cggctggact cagagagcag cccatacctg agcttacaaa tttctccacc    1560
```

```
                                                              -continued tgctaaaaag ccattgacca agattgtctc atacctactg gtggctgagc cggacaagct      1620
ctatgccatg cctcccctg gtatgctga gggggacatc aaggccctga ccactctctg       1680
tgacctggca gaccgagagc ttgtggtcat cattggctgg gccaagcaca tcccaggctt     1740
ctcaagcctc tccctggggg accagatgag cctgctgcag agtgcctgga tggaaatcct    1800
catcctgggc atcgtgtacc gctcgctgcc ctacgacgac aagctggtgt acgctgagga    1860
ctacatcatg gatgaggagc actcccgcct cgcggggctg ctggagctct accgggccat    1920
cctgcagctg gtacgcaggt acaagaagct caaggtggag aaggaggagt ttgtgacgct    1980
caaggccctg gccctcgcca actccgattc catgtacatc gaggatctag aggctgtcca    2040
gaagctgcag gacctgctgc acgaggcact gcaggactac gagctgagcc agcgccatga    2100
ggagccctgg aggacgggca agctgctgct gacactgccg ctgctgcggc agacggccgc    2160
caaggccgtg cagcacttct atagcgtcaa actgcagggc aaagtgccca tgcacaaact    2220
cttcctggag atgctggagg ccaaggcctg ggccagggct gactcccttc aggagtggag    2280
gccactggag caagtgccct ctcccctcca ccgagccacc aagaggcagc atgtgcattt    2340
cctaactccc ttgccccctc ccccatctgt ggcctgggtg ggcactgctc aggctggata    2400
ccacctggag gttttccttc cgcagagggc aggttggcca agagcagctt agaggatctc    2460
ccaaggatga aagaatgtca agccatgatg gaaaatgccc cttccaatca gctgccttca    2520
caagcaggga tcagagcaac tccccgggga tccccaatcc acgcccttct agtccaaccc    2580
ccctcaatga gagaggcagg cagatctcac ccagcactag gacaccagga ggccagggaa    2640
agcatctctg gctcaccatg taacatctgg cttggagcaa gtgggtgttc tgcacaccag    2700
gcagctgcac ctcactggat ctagtgttgc tgcgagtgac ctcacttcag agccctcta    2760 gcagagtggg gcggaagtcc tgatggttgg tgtccatgag gtggaag                   2807
```

<210> SEQ ID NO 2
<211> LENGTH: 500
<212> TYPE: PRT
<213> ORGANISM: Human

<400> SEQUENCE: 2

```
Met Ser Ser Asp Asp Arg His Leu Gly Ser Ser Cys Gly Ser Phe Ile
 1               5                  10                  15

Lys Thr Glu Pro Ser Ser Pro Ser Ser Gly Ile Asp Ala Leu Ser His
            20                  25                  30

His Ser Pro Ser Gly Ser Ser Asp Ala Ser Gly Gly Phe Gly Leu Ala
        35                  40                  45

Leu Gly Thr His Ala Asn Gly Leu Asp Ser Pro Met Phe Ala Gly
    50                  55                  60

Ala Gly Leu Gly Gly Thr Pro Cys Arg Lys Ser Tyr Glu Asp Cys Ala
65                  70                  75                  80

Ser Gly Ile Met Glu Asp Ser Ala Ile Lys Cys Glu Tyr Met Leu Asn
                85                  90                  95

Ala Ile Pro Lys Arg Leu Cys Leu Val Cys Gly Asp Ile Ala Ser Gly
            100                 105                 110

Tyr His Tyr Gly Val Ala Ser Cys Glu Ala Cys Lys Ala Phe Phe Lys
        115                 120                 125

Arg Thr Ile Gln Gly Asn Ile Glu Tyr Ser Cys Pro Ala Thr Asn Glu
    130                 135                 140

Cys Glu Ile Thr Lys Arg Arg Arg Lys Ser Cys Gln Ala Cys Arg Phe
145                 150                 155                 160
```

```
Met Lys Cys Leu Lys Val Gly Met Leu Lys Glu Gly Val Arg Leu Asp
            165                 170                 175
Arg Val Arg Gly Gly Arg Gln Lys Tyr Lys Arg Arg Leu Asp Ser Glu
        180                 185                 190
Ser Ser Pro Tyr Leu Ser Leu Gln Ile Ser Pro Ala Lys Lys Pro
    195                 200                 205
Leu Thr Lys Ile Val Ser Tyr Leu Leu Val Ala Glu Pro Asp Lys Leu
        210                 215                 220
Tyr Ala Met Pro Pro Gly Met Pro Glu Gly Asp Ile Lys Ala Leu
225                 230                 235                 240
Thr Thr Leu Cys Asp Leu Ala Asp Arg Glu Leu Val Val Ile Ile Gly
            245                 250                 255
Trp Ala Lys His Ile Pro Gly Phe Ser Ser Leu Ser Leu Gly Asp Gln
            260                 265                 270
Met Ser Leu Leu Gln Ser Ala Trp Met Glu Ile Leu Ile Leu Gly Ile
        275                 280                 285
Val Tyr Arg Ser Leu Pro Tyr Asp Asp Lys Leu Val Tyr Ala Glu Asp
        290                 295                 300
Tyr Ile Met Asp Glu Glu His Ser Arg Leu Ala Gly Leu Leu Glu Leu
305                 310                 315                 320
Tyr Arg Ala Ile Leu Gln Leu Val Arg Arg Tyr Lys Lys Leu Lys Val
                325                 330                 335
Glu Lys Glu Glu Phe Val Thr Leu Lys Ala Leu Ala Leu Ala Asn Ser
            340                 345                 350
Asp Ser Met Tyr Ile Glu Asp Leu Glu Ala Val Gln Lys Leu Gln Asp
        355                 360                 365
Leu Leu His Glu Ala Leu Gln Asp Tyr Glu Leu Ser Gln Arg His Glu
    370                 375                 380
Glu Pro Trp Arg Thr Gly Lys Leu Leu Leu Thr Leu Pro Leu Leu Arg
385                 390                 395                 400
Gln Thr Ala Ala Lys Ala Val Gln His Phe Tyr Ser Val Lys Leu Gln
                405                 410                 415
Gly Lys Val Pro Met His Lys Leu Phe Leu Glu Met Leu Glu Ala Lys
            420                 425                 430
Ala Trp Ala Arg Ala Asp Ser Leu Gln Glu Trp Arg Pro Leu Glu Gln
        435                 440                 445
Val Pro Ser Pro Leu His Arg Ala Thr Lys Arg Gln His Val His Phe
450                 455                 460
Leu Thr Pro Leu Pro Pro Pro Ser Val Ala Trp Val Gly Thr Ala
465                 470                 475                 480
Gln Ala Gly Tyr His Leu Glu Val Phe Leu Pro Gln Arg Ala Gly Trp
                485                 490                 495
Pro Arg Ala Ala
            500

<210> SEQ ID NO 3
<211> LENGTH: 2985
<212> TYPE: DNA
<213> ORGANISM: Human

<400> SEQUENCE: 3
gcgggccgcc agtgtggtgg aattcggctt gtcactagga gaacatttgt gttaattgca      60
ctgtgctctg tcaaggaaac tttgatttat agctggggtg cacaaataat ggttgccggt     120
```

-continued

| | |
|---|---|
| cgcacatgga ttcggtagaa ctttgccttc ctgaatcttt ttccctgcac tacgaggaag | 180 |
| agcttctctg cagaatgtca aacaaagatc gacacattga ttccagctgt tcgtccttca | 240 |
| tcaagacgga accttccagc ccagcctccc tgacggacag cgtcaaccac cacagccctg | 300 |
| gtggctcttc agacgccagt gggagctaca gttcaaccat gaatggccat cagaacggac | 360 |
| ttgactcgcc acctctctac ccttctgctc ctatcctggg aggtagtggg cctgtcagga | 420 |
| aactgtatga tgactgctcc agcaccattg ttgaagatcc ccagaccaag tgtgaataca | 480 |
| tgctcaactc gatgcccaag agactgtgtt tagtgtgtgg tgacatcgct tctgggtacc | 540 |
| actatgggt agcatcatgt gaagcctgca aggcattctt caagaggaca attcaaggca | 600 |
| atatagaata cagctgccct gccacgaatg aatgtgaaat cacaaagcgc agacgtaaat | 660 |
| cctgccaggc ttgccgcttc atgaagtgtt taaaagtggg catgctgaaa gaagggggtgc | 720 |
| gtcttgacag agtacgtgga ggtcggcaga agtacaagcg caggatagat gcggagaaca | 780 |
| gcccataccc tgaaccctcag ctggttcagc cagccaaaaa gccatataac aagattgtct | 840 |
| cacatttgtt ggtggctgaa ccggagaaga tctatgccat gcctgaccct actgtccccg | 900 |
| acagtgacat caaagccctc actacactgt gtgacttggc cgaccgagag ttggtggtta | 960 |
| tcattggatg ggcgaagcat attccaggct ctccacgct gtccctggcg gaccagatga | 1020 |
| gccttctgca gagtgcttgg atggaaattt tgatccttgg tgtcgtatac cggtctcttt | 1080 |
| catttgagga tgaacttgtc tatgcagacg attatataat ggacgaagac cagtccaaat | 1140 |
| tagcaggcct tcttgatcta ataatgcta tcctgcagct ggtaaagaaa tacaagagca | 1200 |
| tgaagctgga aaagaagaa tttgtcaccc tcaaagctat agctcttgct aattcagact | 1260 |
| ccatgcacat agaagatgtt gaagccgttc agaagcttca ggatgtctta catgaagcgc | 1320 |
| tgcaggatta tgaagctggc cagcacatgg aagaccctcg tcgagctggc aagatgctga | 1380 |
| tgacactgcc actcctgagg cagacctcta ccaaggccgt gcagcatttc tacaacatca | 1440 |
| aactagaagg caaagtccca atgcacaaac ttttttttgga aatgttggag gccaaggtct | 1500 |
| gactaaaagc tccctgggcc ttcccatcct tcatgttgaa aaagggaaaa taaacccaag | 1560 |
| agtgatgtcg aagaaactta gagtttagtt aacaacatca aaaatcaaca gactgcactg | 1620 |
| ataatttagc agcaagacta tgaagcagct ttcagattcc tccataggtt cctgatgagt | 1680 |
| tctttctact ttctccatca tcttctttcc tctttcttcc cacatttctc tttctcttta | 1740 |
| ttttttctcc ttttcttctt tcacctcct tatttctttg cttctttcat tcctagttcc | 1800 |
| cattctcctt tattttcttc ccgtctgcct gccttctttc ttttctttac ctactctcat | 1860 |
| tcctctcttt tctcatcctt cccctttttt ctaaatttga aatagcttta gtttaaaaaa | 1920 |
| aaaaatcctc ccttcccct ttcctttccc tttctttcct ttttccctt ccttttccct | 1980 |
| ttcctttcct ttcctcttga ccttctttcc atctttcttt ttcttccttc tgctgctgaa | 2040 |
| cttttaaaag aggtctctaa ctgaagagag atggaagcca gccctgccaa aggatggaga | 2100 |
| tccataatat ggatgccagt gaacttattg tgaaccatac cgtcccaat gactaaggaa | 2160 |
| tcaaagagag agaaccaacg ttcctaaaag tacagtgcaa catatacaaa ttgactgagt | 2220 |
| gcagtattag atttcatggg agcagcctct aattagacaa cttaagcaac gttgcatcgg | 2280 |
| ctgcttctta tcattgcttt tccatctaga tcagttacag ccatttgatt ccttaattgt | 2340 |
| tttttcaagt cttccaggta tttgttagtt tagctactat gtaactttt cagggaatag | 2400 |
| tttaagcttt attcattcat gcaatactaa agagaaataa gaatactgca attttgtgct | 2460 |
| ggctttgaac aattacgaac aataatgaag gacaaatgaa tcctgaagga agattttttaa | 2520 |

-continued

```
aaatgttttg tttcttctta caaatggaga ttttttttgta ccagctttac cacttttcag    2580
ccatttatta atatgggaat ttaacttact caagcaatag ttgaagggaa ggtgcatatt    2640
atcacggatg caatttatgt tgtgtgccag tctggtccca acatcaatt tcttaacatg     2700 agctccagtt tacctaaatg ttcactgaca caaaggatga gattacacct acagtgactc    2760
tgagtagtca catatataag cactgcacat gagatataga tccgtagaat tgtcaggagt    2820
gcacctctct acttgggagg tacaattgcc atatgatttc tagctgccat ggtggttagg    2880
aatgtgatac tgcctgtttg caaagtcaca gaccttgcct cagaaggagc tgtgagccag    2940
tattcattta agagaattcc accacactgg cggcccgcgc ttgat                   2985
```

<210> SEQ ID NO 4
<211> LENGTH: 458
<212> TYPE: PRT
<213> ORGANISM: Human

<400> SEQUENCE: 4

```
Met Asp Ser Val Glu Leu Cys Leu Pro Glu Ser Phe Ser Leu His Tyr
  1               5                  10                  15

Glu Glu Glu Leu Leu Cys Arg Met Ser Asn Lys Asp Arg His Ile Asp
             20                  25                  30

Ser Ser Cys Ser Ser Phe Ile Lys Thr Glu Pro Ser Ser Pro Ala Ser
         35                  40                  45

Leu Thr Asp Ser Val Asn His His Ser Pro Gly Gly Ser Ser Asp Ala
     50                  55                  60

Ser Gly Ser Tyr Ser Ser Thr Met Asn Gly His Gln Asn Gly Leu Asp
 65                  70                  75                  80

Ser Pro Pro Leu Tyr Pro Ser Ala Pro Ile Leu Gly Gly Ser Gly Pro
                 85                  90                  95

Val Arg Lys Leu Tyr Asp Asp Cys Ser Ser Thr Ile Val Glu Asp Pro
            100                 105                 110

Gln Thr Lys Cys Glu Tyr Met Leu Asn Ser Met Pro Lys Arg Leu Cys
        115                 120                 125

Leu Val Cys Gly Asp Ile Ala Ser Gly Tyr His Tyr Gly Val Ala Ser
    130                 135                 140

Cys Glu Ala Cys Lys Ala Phe Phe Lys Arg Thr Ile Gln Gly Asn Ile
145                 150                 155                 160

Glu Tyr Ser Cys Pro Ala Thr Asn Glu Cys Glu Ile Thr Lys Arg Arg
                165                 170                 175

Arg Lys Ser Cys Gln Ala Cys Arg Phe Met Lys Cys Leu Lys Val Gly
            180                 185                 190

Met Leu Lys Glu Gly Val Arg Leu Asp Arg Val Arg Gly Gly Arg Gln
        195                 200                 205

Lys Tyr Lys Arg Arg Ile Asp Ala Glu Asn Ser Pro Tyr Leu Asn Pro
    210                 215                 220

Gln Leu Val Gln Pro Ala Lys Lys Pro Tyr Asn Lys Ile Val Ser His
225                 230                 235                 240

Leu Leu Val Ala Glu Pro Glu Lys Ile Tyr Ala Met Pro Asp Pro Thr
                245                 250                 255

Val Pro Asp Ser Asp Ile Lys Ala Leu Thr Thr Leu Cys Asp Leu Ala
            260                 265                 270

Asp Arg Glu Leu Val Val Ile Ile Gly Trp Ala Lys His Ile Pro Gly
        275                 280                 285
```

| | | | | | | | | | | |
|---|---|---|---|---|---|---|---|---|---|---|
|Phe|Ser|Thr|Leu|Ser|Leu|Ala|Asp|Gln|Met|Ser|Leu|Leu|Gln|Ser|Ala|
| |290| | | |295| | | |300| |
|Trp|Met|Glu|Ile|Leu|Ile|Leu|Gly|Val|Val|Tyr|Arg|Ser|Leu|Ser|Phe|
|305| | | | |310| | | |315| | | | |320|
|Glu|Asp|Glu|Leu|Val|Tyr|Ala|Asp|Asp|Tyr|Ile|Met|Asp|Glu|Asp|Gln|
| | | | |325| | | | |330| | | | |335|
|Ser|Lys|Leu|Ala|Gly|Leu|Leu|Asp|Leu|Asn|Asn|Ala|Ile|Leu|Gln|Leu|
| | | |340| | | | |345| | | | |350|
|Val|Lys|Lys|Tyr|Lys|Ser|Met|Lys|Leu|Glu|Lys|Glu|Glu|Phe|Val|Thr|
| | | |355| | | | |360| | | | |365|
|Leu|Lys|Ala|Ile|Ala|Leu|Ala|Asn|Ser|Asp|Ser|Met|His|Ile|Glu|Asp|
| |370| | | | |375| | | | |380|
|Val|Glu|Ala|Val|Gln|Lys|Leu|Gln|Asp|Val|Leu|His|Glu|Ala|Leu|Gln|
|385| | | | |390| | | | |395| | | | |400|
|Asp|Tyr|Glu|Ala|Gly|Gln|His|Met|Glu|Asp|Pro|Arg|Arg|Ala|Gly|Lys|
| | | | |405| | | | |410| | | | |415|
|Met|Leu|Met|Thr|Leu|Pro|Leu|Leu|Arg|Gln|Thr|Ser|Thr|Lys|Ala|Val|
| | | |420| | | | |425| | | | |430|
|Gln|His|Phe|Tyr|Asn|Ile|Lys|Leu|Glu|Gly|Lys|Val|Pro|Met|His|Lys|
| | | |435| | | | |440| | | | |445|
|Leu|Phe|Leu|Glu|Met|Leu|Glu|Ala|Lys|Val|
| | | |450| | | | |455|

<210> SEQ ID NO 5
<211> LENGTH: 2987
<212> TYPE: DNA
<213> ORGANISM: Human

<400> SEQUENCE: 5

```
gcgggccgcc agtgtggtgg aattcggctt gtcactagga gaacatttgt gttaattgca      60
ctgtgctctg tcaaggaaac tttgatttat agctggggtg cacaaataat ggttgccggt     120
cgcacatgga ttcggtagaa ctttgccttc ctgaatcttt ttccctgcac tacgaggaag     180
agcttctctg cagaatgtca acaaagatc gacacattga ttccagctgt tcgtccttca      240
tcaagacgga accttccagc ccagcctccc tgacggacag cgtcaaccac acagccctg      300
gtggctcttc agacgccagt gggagctaca gttcaaccat gaatggccat cagaacggac     360
ttgactcgcc acctctctac ccttctgctc ctatcctggg aggtagtggg cctgtcagga     420
aactgtatga tgactgctcc agcaccattg ttgaagatcc ccagaccaag tgtgaataca     480
tgctcaactc gatgcccaag agactgtgtt tagtgtgtgg tgacatcgct tctgggtacc     540
actatgggt agcatcatgt gaagcctgca aggcattctt caagaggaca attcaaggca     600
atatagaata cagctgccct gccacgaatg aatgtgaaat cacaaagcgc agacgtaaat     660
cctgccagc ttgccgcttc atgaagtgtt taaaagtggg catgctgaaa gaagggggtgc     720
gtcttgacag agtacgtgga ggtcggcaga agtacaagcg caggatagat gcggagaaca     780
gcccatacct gaaccctcag ctggttcagc agccaaaaa gccatataac aagattgtct     840
cacatttgtt ggtggctgaa ccggagaaga tctatgccat gcctgaccct actgtccccg     900
acagtgacat caaagccctc actacactgt gtgacttggc cgaccgagag ttggtggtta     960
tcattggatg ggcgaagcat attccaggct ctccacgct gtccctggcg gaccagatga    1020
gccttctgca gagtgcttgg atggaaattt tgatccttgg tgtcgtatac cggtctcttt    1080
catttgagga tgaacttgtc tatgcagacg attatataat ggacgaagac cagtccaaat    1140
```

-continued

```
tagcaggcct tcttgatcta aataatgcta tcctgcagct ggtaaagaaa tacaagagca      1200
tgaagctgga aaagaagaa tttgtcaccc tcaaagctat agctcttgct aattcagact      1260
ccatgcacat agaagatgtt gaagccgttc agaagcttca ggatgtctta catgaagcgc      1320
tgcaggatta tgaagctggc cagcacatgg agaagaccct cgtcgagctg caagatgct       1380 gatgacactg ccactcctga ggcagacctc taccaaggcc gtgcagcatt tctacaacat      1440
caaactagaa ggcaaagtcc caatgcacaa acttttttg gaaatgttgg aggccaaggt       1500
ctgactaaaa gctccctggg ccttcccatc cttcatgttg aaaagggaa aataaaccca       1560 agagtgatgt cgaagaaact tagagtttag ttaacaacat caaaaatcaa cagactgcac      1620
tgataattta gcagcaagac tatgaagcag cttcagatt cctccatagg ttcctgatga       1680
gttctttcta ctttctccat catcttcttt cctctttctt cccacatttc tctttctctt      1740
tattttttct cctttcttc tttcacctcc cttatttctt tgcttctttc attcctagtt       1800
cccattctcc tttatttct tcccgtctgc ctgccttctt tcttttcttt acctactctc       1860
attcctctct tttctcatcc ttcccctttt ttctaaattt gaaatagctt tagtttaaaa      1920
aaaaaaatcc tcccttcccc cttcctttc ctttctttc cttttccct ttccttttcc         1980 ctttcctttc ctttctctt gaccttcttt ccatctttct ttttcttcct tctgctgctg       2040 aactttaaa agaggtctct aactgaagag agatggaagc cagccctgcc aaaggatgga       2100
gatccataat atggatgcca gtgaacttat tgtgaaccat accgtcccca atgactaagg      2160
aatcaaagag agagaaccaa cgttcctaaa agtacagtgc aacatataca aattgactga      2220
gtgcagtatt agatttcatg ggagcagcct ctaattagac aacttaagca acgttgcatc      2280
ggctgcttct tatcattgct tttccatcta gatcagttac agccatttga ttccttaatt      2340
gttttttcaa gtcttccagg tatttgttag tttagctact atgtaacttt tcagggaat       2400 agtttaagct ttattcattc atgcaatact aaagagaaat aagaatactg caattttgtg      2460
ctggctttga acaattacga acaataatga aggacaaatg aatcctgaag gaagattttt      2520
aaaaatgttt tgtttcttct tacaaatgga gattttttg taccagcttt accacttttc      2580
agccatttat taatatggga atttaactta ctcaagcaat agttgaaggg aaggtgcata      2640
ttatcacgga tgcaatttat gttgtgtgcc agtctggtcc caaacatcaa tttcttaaca      2700
tgagctccag tttacctaaa tgttcactga cacaaaggat gagattacac ctacagtgac      2760
tctgagtagt cacatatata agcactgcac atgagatata gatccgtaga attgtcagga      2820
gtgcacctct ctacttggga ggtacaattg ccatatgatt tctagctgcc atggtggtta      2880
ggaatgtgat actgcctgtt tgcaaagtca cagaccttgc ctcagaagga gctgtgagcc      2940
agtattcatt taagagaatt ccaccacact ggcggcccgc gcttgat                    2987
```

<210> SEQ ID NO 6
<211> LENGTH: 418
<212> TYPE: PRT
<213> ORGANISM: Human

<400> SEQUENCE: 6

```
Met Asp Ser Val Glu Leu Cys Leu Pro Glu Ser Phe Ser Leu His Tyr
 1               5                  10                  15

Glu Glu Glu Leu Leu Cys Arg Met Ser Asn Lys Asp Arg His Ile Asp
            20                  25                  30

Ser Ser Cys Ser Ser Phe Ile Lys Thr Glu Pro Ser Ser Pro Ala Ser
        35                  40                  45
```

```
Leu Thr Asp Ser Val Asn His His Ser Pro Gly Gly Ser Ser Asp Ala
 50                  55                  60

Ser Gly Ser Tyr Ser Ser Thr Met Asn Gly His Gln Asn Gly Leu Asp
 65                  70                  75                  80

Ser Pro Pro Leu Tyr Pro Ser Ala Pro Ile Leu Gly Gly Ser Gly Pro
                 85                  90                  95

Val Arg Lys Leu Tyr Asp Asp Cys Ser Ser Thr Ile Val Glu Asp Pro
                100                 105                 110

Gln Thr Lys Cys Glu Tyr Met Leu Asn Ser Met Pro Lys Arg Leu Cys
                115                 120                 125

Leu Val Cys Gly Asp Ile Ala Ser Gly Tyr His Tyr Gly Val Ala Ser
     130                 135                 140

Cys Glu Ala Cys Lys Ala Phe Phe Lys Arg Thr Ile Gln Gly Asn Ile
 145                 150                 155                 160

Glu Tyr Ser Cys Pro Ala Thr Asn Glu Cys Glu Ile Thr Lys Arg Arg
                165                 170                 175

Arg Lys Ser Cys Gln Ala Cys Arg Phe Met Lys Cys Leu Lys Val Gly
                180                 185                 190

Met Leu Lys Glu Gly Val Arg Leu Asp Arg Val Arg Gly Gly Arg Gln
     195                 200                 205

Lys Tyr Lys Arg Arg Ile Asp Ala Glu Asn Ser Pro Tyr Leu Asn Pro
 210                 215                 220

Gln Leu Val Gln Pro Ala Lys Lys Pro Tyr Asn Lys Ile Val Ser His
225                 230                 235                 240

Leu Leu Val Ala Glu Pro Glu Lys Ile Tyr Ala Met Pro Asp Pro Thr
                245                 250                 255

Val Pro Asp Ser Asp Ile Lys Ala Leu Thr Thr Leu Cys Asp Leu Ala
                260                 265                 270

Asp Arg Glu Leu Val Val Ile Gly Trp Ala Lys His Ile Pro Gly
                275                 280                 285

Phe Ser Thr Leu Ser Leu Ala Asp Gln Met Ser Leu Leu Gln Ser Ala
 290                 295                 300

Trp Met Glu Ile Leu Ile Leu Gly Val Val Tyr Arg Ser Leu Ser Phe
305                 310                 315                 320

Glu Asp Glu Leu Val Tyr Ala Asp Tyr Ile Met Asp Glu Asp Gln
                325                 330                 335

Ser Lys Leu Ala Gly Leu Leu Asp Leu Asn Asn Ala Ile Leu Gln Leu
                340                 345                 350

Val Lys Lys Tyr Lys Ser Met Lys Leu Glu Lys Glu Glu Phe Val Thr
                355                 360                 365

Leu Lys Ala Ile Ala Leu Ala Asn Ser Asp Ser Met His Ile Glu Asp
     370                 375                 380

Val Glu Ala Val Gln Lys Leu Gln Asp Val Leu His Glu Ala Leu Gln
385                 390                 395                 400

Asp Tyr Glu Ala Gly Gln His Met Glu Lys Thr Leu Val Glu Leu Ala
                405                 410                 415

Arg Cys

<210> SEQ ID NO 7
<211> LENGTH: 403
<212> TYPE: DNA
<213> ORGANISM: Human

<400> SEQUENCE: 7
```

```
cttttttagga ggtggagaaa tttgtaagct caggtatggg ctgctctctg agtccagccg      60
tcgcttgtat ttctgacggc ctccacgcac tcgatcaagg cgcacacctt ccttcagcat     120
ccccactttg aggcatttca tgaagcggca ggcctggcag gacttgcgcc tccgtttggt     180
gatctcgcac tcgttggtgg ccgggcagct gtactcaatg ttcccttgga tagtcctctt     240
gaagaaggcc ttgcaagcct cgcaggaggc ccacgcgtna gtggtagcca gagnaaatgt     300
ccccgcacac gaggcacagg cgcttgggga tggcgttgag catgttactt cgcacttgga     360
tgggccgagt cctccatgga tggccgctgg caacagttcc tcg                       403
```

```
<210> SEQ ID NO 8
<211> LENGTH: 622
<212> TYPE: DNA
<213> ORGANISM: Human

<400> SEQUENCE: 8
```

```
cnnnnnnnnn nnnttttnnt gcctaaagtg gtacccngaa gngatgtcac cacacactaa      60
acacagtctc ttgggcatcg agttgagcat gtattcacac ttggtctggg gatcttcaac     120
aatggtgctg gagcagtcat catacagttt cctgacaggc ccactacctc ccaggatagg     180
agcagaaggg tagagaggtg gcgagtcaag tccgttctga tggccattca tggttgaact     240
gtagctccca ctggcgtctg aagagccacc agggctgtgg tggttgacgc tgtccgtcag     300
ggaggctggg ctggaaggtt ccgtcttgat gaaggacgaa cagctggaat caatgtgtcg     360
atctttgttt ggacattctg cagagaagct cttcctccgt ngtgcaggga aaagattca      420 ggaaggcaaa gttcttcccg aatccatgtg cgaccggaaa ccattatttg ngcaccccag     480
ctattaatca aagttccttg acagagacag gcaattaca naatgtctcc tntnggggat      540
caactgttcn gtattnnnnn nnnnnnnnnn nnnnnnnnnn nnnnnnnnnn nnnnnnnnnn     600
nnnnnnnnnn nnnnnnnnnn tt                                              622
```

```
<210> SEQ ID NO 9
<211> LENGTH: 22
<212> TYPE: DNA
<213> ORGANISM: Artificial Sequence
<220> FEATURE:
<223> OTHER INFORMATION: oligonucleotide

<400> SEQUENCE: 9
tgagtccagc cgtcgcttgt at                                               22

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
tgcaagcctc gcaggaggcc                                                  20

<210> SEQ ID NO 11
<211> LENGTH: 22
<212> TYPE: DNA
<213> ORGANISM: Artificial Sequence
<220> FEATURE:
<223> OTHER INFORMATION: oligonucleotide

<400> SEQUENCE: 11
ggccttcttc aagaggacta tc                                               22
```

<210> SEQ ID NO 12
<211> LENGTH: 21
<212> TYPE: DNA
<213> ORGANISM: Artificial Sequence
<220> FEATURE:
<223> OTHER INFORMATION: oligonucleotide

<400> SEQUENCE: 12
aaagatcgac acattgattc c                                             21

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
gacttgactc gccacctctc                                               20

<210> SEQ ID NO 14
<211> LENGTH: 21
<212> TYPE: DNA
<213> ORGANISM: Artificial Sequence
<220> FEATURE:
<223> OTHER INFORMATION: oligonucleotide

<400> SEQUENCE: 14
gttctgatgg ccattcatgg t                                             21

<210> SEQ ID NO 15
<211> LENGTH: 21
<212> TYPE: DNA
<213> ORGANISM: Artificial Sequence
<220> FEATURE:
<223> OTHER INFORMATION: oligonucleotide

<400> SEQUENCE: 15
gaatatgatg accctaatgc a                                             21

<210> SEQ ID NO 16
<211> LENGTH: 21
<212> TYPE: DNA
<213> ORGANISM: Artificial Sequence
<220> FEATURE:
<223> OTHER INFORMATION: oligonucleotide

<400> SEQUENCE: 16
cttccacctc atggacacca a                                             21

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
gttaattgca ctgtgctctg                                               20

<210> SEQ ID NO 18
<211> LENGTH: 20
<212> TYPE: DNA
<213> ORGANISM: Artificial Sequence
<220> FEATURE:

```
<223> OTHER INFORMATION: oligonucleotide

<400> SEQUENCE: 18
agtgtggtgg aattctctta                                              20

<210> SEQ ID NO 19
<211> LENGTH: 21
<212> TYPE: DNA
<213> ORGANISM: Artificial Sequence
<220> FEATURE:
<223> OTHER INFORMATION: oligonucleotide

<400> SEQUENCE: 19
tctagtgttg ctgcgagtga c                                            21

<210> SEQ ID NO 20
<211> LENGTH: 21
<212> TYPE: DNA
<213> ORGANISM: Artificial Sequence
<220> FEATURE:
<223> OTHER INFORMATION: oligonucleotide

<400> SEQUENCE: 20
cttccacctc atggacacca a                                            21

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
gtctgactaa aagctccctg                                              20

<210> SEQ ID NO 22
<211> LENGTH: 21
<212> TYPE: DNA
<213> ORGANISM: Artificial Sequence
<220> FEATURE:
<223> OTHER INFORMATION: oligonucleotide

<400> SEQUENCE: 22
gaagatgatg gagaaagtag a                                            21

<210> SEQ ID NO 23
<211> LENGTH: 20
<212> TYPE: DNA
<213> ORGANISM: Artificial Sequence
<220> FEATURE:
<223> OTHER INFORMATION: oligonucleotide

<400> SEQUENCE: 23
cattccacgg aggcatcctc                                              20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
ccaaggccgt gcagcacttc                                              20
```

```
<210> SEQ ID NO 25
<211> LENGTH: 21
<212> TYPE: DNA
<213> ORGANISM: Artificial Sequence
<220> FEATURE:
<223> OTHER INFORMATION: oligonucleotide

<400> SEQUENCE: 25
gacagcctct agatcctcga t                                              21

<210> SEQ ID NO 26
<211> LENGTH: 21
<212> TYPE: DNA
<213> ORGANISM: Artificial Sequence
<220> FEATURE:
<223> OTHER INFORMATION: oligonucleotide

<400> SEQUENCE: 26
atcatggctt gacattcttt c                                              21

<210> SEQ ID NO 27
<211> LENGTH: 19
<212> TYPE: DNA
<213> ORGANISM: Artificial Sequence
<220> FEATURE:
<223> OTHER INFORMATION: oligonucleotide

<400> SEQUENCE: 27
agctcttgct aattcagac                                                 19

<210> SEQ ID NO 28
<211> LENGTH: 21
<212> TYPE: DNA
<213> ORGANISM: Artificial Sequence
<220> FEATURE:
<223> OTHER INFORMATION: oligonucleotide

<400> SEQUENCE: 28
tcaacatgaa ggatgggaag g                                              21

<210> SEQ ID NO 29
<211> LENGTH: 2807
<212> TYPE: DNA
<213> ORGANISM: Human

<400> SEQUENCE: 29
cttatactac tgggattacg ttgttataga ttgtatgata ggctcgaagc cagtaaacct    60
tcttgacgtc taaaggagg aagtttaat ttcagtccaa tacctcttgt acatacgata    120
caagaactaa cgaagcgact tcttcgtaac tttatataac caaagtggac cttttccggt   180
tatatgggtc atcttcttaa tcttcttctt tcgcaacgtc ttctactacg tcttaattgt   240
aatttatttc acctacttct taaacacctt cttctctgtc tattacttct tttgaaataa   300
ctagagttgc aaaatttccg ggtctgtata gtgaacctat acttgctctg acggtttgtt   360
cttctataaa accttaggtg ttgtctacga cgtcttacct cggatcttca ccttgcacat   420
gatggcgttg actttcagtg ctaatcctga ctgttattcc taacctctta ggtacaactg   480
gtttacgtgg tcgtgtcttc accttaactt agacgagatt tcctctggtt ccctaaaaac   540
ctgtttgagg tattacttta atgatcctga aaccttttct agtcgtcggc tcttttcatg   600
tagttgttag tcggccctcg ggtacctcgt gacaggagtc tctacgcgtc caatccgagt   660
gacagatccg gtccgggtgg aatcagtgac acctgaccgt taccttcgag aaggacctgt   720
```

-continued

```
gtggacggga tcgggagtgg gaccccacct tctctttact cgaaccgaac gttgagtctg      780
gtaaggtgcc tccgtaggag gggaagggac ccgaccactt attttcaaag gactccagtt      840
cctgaaggaa aagggacggt tttaccacag gtcttgaaac tccggtctcc actaggtcac      900
taaaccctcg acgtccagtg tgtccgacga gtctcccgac gacttgtcct acaggagcct      960
gctgtccgtg gacccgaggt cgacgccgag gaagtagttc tgactcggca ggtcgggcag     1020
gagcccgtat ctacgggagt cggtggtgtc ggggtcaccg agcaggctgc ggtcgccgcc     1080
gaaaccggac cggacccgt gggtgcggtt gccagacctg agcggtgggt acaaacgtcc      1140
gcggcccgac cctccgtggg gtacggcgtt ctcgatgctc ctgacacggt cgccgtagta     1200
cctcctgagc cggtagttca cgctcatgta cgagttgcgg taggggttcg cggacacgga     1260
gcacacgccc ctgtaacgga gaccgatggt gatgccgcac cggaggacgc tccgaacgtt     1320
ccggaagaag ttctcctgat aggttccctt gtaactcatg tcgacgggcc ggtgggttgct    1380 cacgctctag tggttttgcct ccgcgttcag gacggtccga acggcgaagt actttacgga    1440
gtttcacccc tacgacttcc ttccacacgc ggaactagct cacgcacctc cggcagtctt     1500
tatgttcgct gccgacctga gtctctcgtc gggtatggac tcgaatgttt aaagaggtgg     1560 acgattttc ggtaactggt tctaacagag tatggatgac caccgactcg gcctgttcga      1620
gatacggtac ggaggggggac catacggact cccctgtag ttccgggact ggtgagagac      1680
actggaccgt ctggctctcg aacaccagta gtaaccgacc cggttcgtgt agggtccgaa     1740
gagttcggag agggaccccc tggtctactc ggacgacgtc tcacggacct acctttagga     1800
gtaggacccg tagcacatgg cgagcgacgg gatgctgctg ttcgaccaca tgcgactcct     1860
gatgtagtac ctactcctcg tgagggcgga gcgccccgac gacctcgaga tggcccggta     1920
ggacgtcgac catgcgtcca tgttcttcga gttccacctc ttcctcctca aacactgcga     1980
gttccgggac cgggagcgt tgaggctaag gtacatgtag ctcctagatc tccgacaggt      2040
cttcgacgtc ctggacgacg tgctccgtga cgtcctgatg ctcgactcgg tcgcggtact    2100
cctcgggacc tcctgcccgt tcgacgacga ctgtgacggc gacgacgccg tctgccggcg     2160
gttccggcac gtcgtgaaga tatcgcagtt tgacgtcccg tttcacgggt acgtgtttga     2220
gaaggacctc tacgacctcc ggttccggac ccggtcccga ctgagggaag tcctcacctc     2280
cggtgacctc gttcacggga gaggggaggt ggctcggtgg ttctccgtcg tacacgtaaa     2340
ggattgaggg aacgggggag ggggtagaca ccggacccac ccgtgacgag tccgacctat     2400
ggtggacctc caaaaggaag gcgtctcccg tccaaccggt tctcgtcgaa tctcctagag     2460
ggttcctact ttcttacagt tcggtactac cttttacggg gaaggttagt cgacggaagt     2520
gttcgtccct agtctcgttg agggggcccct agggggttagg tgcgggaaga tcaggttggg    2580
gggagttact ctctccgtcc gtctagagtg ggtcgtgatc ctgtggtcct ccggtccctt     2640
tcgtagagac cgagtggtac attgtagacc gaacctcgtt cacccacaag acgtgtggtc     2700
cgtcgacgtg gagtgaccta gatcacaacg acgctcactg gagtgaagtc tcggggagat     2760
cgtctcaccc cgccttcagg actaccaacc acaggtactc caccttc                  2807
```

<210> SEQ ID NO 30
<211> LENGTH: 2985
<212> TYPE: DNA
<213> ORGANISM: Human

<400> SEQUENCE: 30

```
cgcccggcgg tcacaccacc ttaagccgaa cagtgatcct cttgtaaaca caattaacgt       60
```

-continued

```
gacacgagac agttcctttg aaactaaata tcgaccccac gtgtttatta ccaacggcca    120
gcgtgtacct aagccatctt gaaacggaag gacttagaaa aagggacgtg atgctccttc    180
tcgaagagac gtcttacagt ttgtttctag ctgtgtaact aaggtcgaca agcaggaagt    240
agttctgcct tggaaggtcg ggtcggaggg actgcctgtc gcagttggtg gtgtcgggac    300
caccgagaag tctgcggtca ccctcgatgt caagttggta cttaccggta gtcttgcctg    360
aactgagcgg tggagagatg ggaagacgag gataggaccc tccatcaccc ggacagtcct    420
ttgacatact actgacgagg tcgtggtaac aacttctagg ggtctggttc acacttatgt    480
acgagttgag ctacgggttc tctgacacaa atcacacacc actgtagcga agacccatgg    540
tgataccccca tcgtagtaca cttcggacgt tccgtaagaa gttctcctgt taagttccgt    600
tatatcttat gtcgacggga cggtgcttac ttacactttta gtgtttcgcg tctgcattta    660
ggacggtccg aacggcgaag tacttcacaa attttcaccc gtacgacttt cttccccacg    720
cagaactgtc tcatgcacct ccagccgtct tcatgttcgc gtcctatcta cgcctcttgt    780
cgggtatgga cttgggagtc gaccaagtcg gtcggttttt cggtatattg ttctaacaga    840
gtgtaaacaa ccaccgactt ggcctcttct agatacggta cggactggga tgacaggggc    900
tgtcactgta gtttcgggag tgatgtgaca cactgaaccg gctggctctc aaccaccaat    960
agtaacctac ccgcttcgta taaggtccga agaggtgcga cagggaccgc ctggtctact   1020
cggaagacgt ctcacgaacc tacctttaaa actaggaacc acagcatatg gccagagaaa   1080
gtaaactcct acttgaacag atacgtctgc taatatatta cctgcttctg gtcaggttta   1140
atcgtccgga agaactagat ttattacgat aggacgtcga ccatttcttt atgttctcgt   1200
acttcgacct tttttcttctt aaacagtggg agtttcgata tcgagaacga ttaagtctga   1260
ggtacgtgta tcttctacaa cttcggcaag tcttcgaagt cctacagaat gtacttcgcg   1320
acgtcctaat acttcgaccg gtcgtgtacc ttctgggagc agctcgaccg ttctacgact   1380
actgtgacgg tgaggactcc gtctggagat ggttccggca cgtcgtaaag atgttgtagt   1440
ttgatcttcc gtttcagggt tacgtgtttg aaaaaaacct ttacaacctc cggttccaga   1500
ctgatttttcg agggacccgg aagggtagga agtacaactt tttccctttt atttgggttc   1560
tcactacagc ttctttgaat ctcaaatcaa ttgttgtagt ttttagttgt ctgacgtgac   1620
tattaaatcg tcgttctgat acttcgtcga aagtctaagg aggtatccaa ggactactca   1680
agaaagatga aagaggtagt agaagaaagg agaaagaagg gtgtaaagag aaagagaaat   1740
aaaaaagagg aaaagaagaa agtggaggga ataaagaaac gaagaaagta aggatcaagg   1800
gtaagaggaa ataaaagaag ggcagacgga cggaagaaag aaaagaaatg gatgagagta   1860
aggagagaaa agagtaggaa ggggaaaaaa gatttaaact ttatcgaaat caaatttttt   1920
tttttaggag ggaaggggga aaggaaaggg aagaaaggga aaaagggaaa ggaaaaggga   1980
aaggaaagga aaggagaact ggaagaaagg tagaaagaaa aagaaggaag acgacgactt   2040
gaaaattttc tccagagatt gacttctctc taccttcggt cgggacggtt tcctacctct   2100
aggtattata cctacggtca cttgaataac acttggtatg gcagggggtta ctgattcctt   2160
agtttctctc tcttggttgc aaggattttc atgtcacgtt gtatatgttt aactgactca   2220
cgtcataatc taaagtaccc tcgtcggaga ttaatctgtt gaattcgttg caacgtagcc   2280
gacgaagaat agtaacgaaa aggtagatct agtcaatgtc ggtaaactaa ggaattaaca   2340
aaaaagttca gaaggtccat aaacaatcaa atcgatgata cattgaaaaa gtcccttatc   2400
```

-continued

| aaattcgaaa | taagtaagta | cgttatgatt | tctctttatt | cttatgacgt | taaaacacga | 2460 |
| ccgaaacttg | ttaatgcttg | ttattacttc | ctgtttactt | aggacttcct | tctaaaaatt | 2520 |
| tttacaaaac | aaagaagaat | gtttacctct | aaaaaaacat | ggtcgaaatg | gtgaaaagtc | 2580 |
| ggtaaataat | tataccctta | aattgaatga | gttcgttatc | aacttccctt | ccacgtataa | 2640 |
| tagtgcctac | gttaaataca | acacacggtc | agaccagggt | ttgtagttaa | agaattgtac | 2700 |
| tcgaggtcaa | atggatttac | aagtgactgt | gtttcctact | ctaatgtgga | tgtcactgag | 2760 |
| actcatcagt | gtatatattc | gtgacgtgta | ctctatatct | aggcatctta | acagtcctca | 2820 |
| cgtggagaga | tgaaccctcc | atgttaacgg | tatactaaag | atcgacggta | ccaccaatcc | 2880 |
| ttacactatg | acggacaaac | gtttcagtgt | ctggaacgga | gtcttcctcg | acactcggtc | 2940 |
| ataagtaaat | tctcttaagg | tggtgtgacc | gccgggcgcg | aacta | | 2985 |

What is claimed:

1. A purified DNA molecule encoding a human nNR1 protein wherein said protein comprises the amino acid sequence as follows:

MSSDDRHLGS SCGSFIKTEP SSPSSGIDAL SHHSPSGSSD

ASGGFGLALG THANGLDSPP MFAGAGLGGT PCRKSYEDCA

SGIMEDSAIK CEYMLNAIPK RLCLVCGDIA SGYHYGVASC

EACKAFFKRT IQGNIEYSCP ATNECEITKR RRKSCQACRF

MKCLKVGMLK EGVRLDRVRG GRQKYKRRLD SESSPYLSLQ

ISPPAKKPLT KIVSYLLVAE PDKLYAMPPP GMPEGDIKAL

TTLCDLADRE LVVIIGWAKH IPGFSSLSLG DQMSLLQSAW

MEILILGIVY RSLPYDDKLV YAEDYIMDEE HSRLAGLLEL

YRAILQLVRR YKKLKVEKEE FVTLKALALA NSDSMYIEDL

EAVQKLQDLL HEALQDYELS QRHEEPWRTG KLLLTLPLLR

QTAAKAVQHF YSVKLQGKVP MHKLFLEMLE AKAWAAADSL

QEWRPLEQVP SPLHRATKRQ HVHFLTPLPP PPSVAWVGTA

QAGYHLEVFL PQRAGWPRAA, as set forth in three-letter abbreviation in SEQ ID NO:2.

2. An expression vector for expressing a human nNR1 protein in a recombinant host cell wherein said expression vector comprises the DNA molecule of claim 1.

3. A host cell which expresses a recombinant human nNR1 protein wherein said host cell contains the expression vector of claim 2.

4. A process for expressing a human nNR1 protein in a recombinant host cell, comprising:

(a) transfecting the expression vector of claim 2 into a suitable host cell; and, (b) culturing the host cells of step (a) under conditions which allow expression of said the human nNR1 protein from said expression vector.

5. A purified DNA molecule encoding a human nNR1 protein wherein said protein consists of the amino acid sequence as follows:

MSSDDRHLGS SCGSFIKTEP SSPSSGIDAL SHHSPSGSSD

ASGGFGLALG THANGLDSPP MFAGAGLGGT PCRKSYEDCA

SGIMEDSAIK CEYMLNAIPK RLCLVCGDIA SGYHYGVASC

EACKAFFKRT IQGNIEYSCP ATNECEITKR RRKSCQACRF

MKCLKVGMLK EGVRLDRVRG GRQKYKRRLD SESSPYLSLQ

ISPPAKKPLT KIVSYLLVAE PDKLYAMPPP GMPEGDIKAL

TTLCDLADPE LVVIIGWAKH IPGFSSLSLG DQMSLLQSAW

MEILILGIVY RSLPYDDKLV YAEDYIMDEE HSRLAGLLEL

YRAILQLVRR YKKLKVEKEE FVTLKAAALA NSDSMYIEDL

EAVQKLQDLL HEALQDYELS QRHEEPWRTC KLLLTLPLLR

QTAAKAVQHF YSVKLQGKVP MHKLFLEMLE AKAWARADSL

QEWRPLEQVP SPLHRATKRQ HVHFLTPLPP PPSVAWVGTA

QAGYHLEVFL PQRAGWPRAA as set forth in three-letter abbreviation in SEQ ID NO:2.

6. An expression vector for expressing a human nNR1 protein in a recombinant host cell wherein said expression vector comprises the DNA molecule of claim 5.

7. A host cell which expresses a recombinant human nNR1 protein wherein said host cell contains the expression vector of claim 6.

8. A process for expressing a human nNR1 protein in a recombinant host cell, comprising:

(a) transfecting the expression vector of claim 6 into a suitable host cell; and, (b) culturing the host cells of step (a) under conditions which allow expression of said the human nNR1 protein from said expression vector.

9. A purified DNA molecule encoding a human nNR1 protein wherein said DNA molecule comprises the nucleotide sequence as set forth in SEQ ID NO:1, as follows:

(SEQ ID NO:1)

```
GAATATGATG ACCCTAATGC AACAATATCT AACATACTAT
CCGAGCTTCG GTCATTTGGA AGAACTGCAG ATTTTCCTCC
TTCAAAATTA AAGTCAGGTT ATGGAGAACA TGTATGCTAT
GTTCTTGATT GCTTCGCTGA AGAAGCATTG AAATATATTG
GTTTCACCTG GAAAAGGCCA ATATACCCAG TAGAAGAATT
AGAAGAAGAA AGCGTTGCAG AAGATGATGC AGAATTAACA
TTAAATAAAG TGGATGAAGA ATTTGTGGAA GAAGAGACAG
ATAATGAAGA AAACTTTATT GATCTCAACG TTTTAAAGGC
CCAGACATAT CACTTGGATA TGAACGAGAC TGCCAAACAA
GAAGATATTT TGGAATCCAC AACAGATGCT GCAGAATGGA
GCCTAGAAGT GGAACGTGTA CTACCGCAAC TGAAAGTCAC
GATTAGGACT GACAATAAGG ATTGGAGAAT CCATGTTGAC
CAAATGCACC AGCACAGAAG TGGAATTGAA TCTGCTCTAA
AGGAGACCAA GGGATTTTTG GACAAACTCC ATAATGAAAT
TACTAGGACT TTGGAAAAGA TCAGCAGCCG AGAAAAGTAC
ATCAACAATC AGCCGGGAGC CCATGGAGCA CTGTCCTCAG
AGATGCGCAG GTTAGGCTCA CTGTCTAGGC AGGCCCACC
TTAGTCACTG TGGACTGGCA ATGGAAGCTC TTCCTGGACA
CACCTGCCCT AGCCCTCACC CTGGGGTGGA AGAGAAATGA
GCTTGGCTTG CAACTCAGAC CATTCCACGG AGGCATCCTC
CCCTTCCCTG GGCTGGTGAA TAAAAGTTTC CTGAGGTCAA
GGACTTCCTT TTCCCTGCCA AAATGGTGTC CAGAACTTTG
AGGCCAGAGG TGATCCAGTG ATTTGGGAGC TGCAGGTCAC
ACAGGCTGCT CAGAGGGCTG CTGAACAGGA TGTCCTCGGA
CGACAGGCAC CTGGGCTCCA GCTGCGGCTC CTTCATCAAG
ACTGAGCCGT CCAGCCCGTC CTCGGGCATA GATGCCCTCA
GCCACCACAG CCCCAGTGGC TCGTCCGACG CCAGCGGCGG
CTTTGGCCTG GCCCTGGGCA CCCACGCCAA CGGTCTGGAC
TCGCCACCCA TGTTTGCAGG CGCCGGGCTG GGAGGCACCC
CATGCCGCAA GAGCTACGAG GACTGTGCCA GCGGCATCAT
GGAGGACTCG GCCATCAAGT GCGAGTACAT GCTCAACGCC
ATCCCCAAGC GCCTGTGCCT CGTGTGCGGG GACATTGCCT
CTGGCTACCA CTACGGCGTG GCCTCCTGCG AGGCTTGCAA
GGCCTTCTTC AAGAGGACTA TCCAAGGGAA CATTGAGTAC
AGCTGCCCGG CCACCAACGA GTGCGAGATC ACCAAACGGA
GGCGCAAGTC CTGCCAGGCC TGCCGCTTCA TGAAATGCCT
CAAAGTGGGG ATGCTGAAGG AAGGTGTGCG CCTTGATCGA
GTGCGTGGAG GCCGTCAGAA ATACAAGCGA CGGCTGGACT
CAGAGAGCAG CCCATACCTG AGCTTACAAA TTTCTCCACC
TGCTAAAAAG CCATTGACCA AGATTGTCTC ATACCTACTG
```

-continued

```
GTGGCTGAGC CGGACAAGCT CTATGCCATG CCTCCCCCTG
GTATGCCTGA GGGGGACATC AAGGCCCTGA CCACTCTCTG
TGACCTGGCA GACCGAGAGC TTGTGGTCAT CATTGGCTGG
GCCAAGCACA TCCCAGGCTT CTCAAGCCTC TCCCTGGGGG
ACCAGATGAG CCTGCTGCAG AGTGCCTGGA TGGAAATCCT
CATCCTGGGC ATCGTGTACC GCTCGCTGCC CTACGACGAC
AAGCTGGTGT ACGCTGAGGA CTACATCATG GATGAGGAGC
ACTCCCGCCT CGCGGGGCTG CTGGAGCTCT ACCGGGCCAT
CCTGCAGCTG GTACGCAGGT ACAAGAAGCT CAAGGTGGAG
AAGGAGGAGT TTGTGACGCT CAAGGCCCTG GCCCTCGCCA
ACTCCGATTC CATGTACATC GAGGATCTAG AGGCTGTCCA
GAAGCTGCAG GACCTGCTGC ACGAGGCACT GCAGGACTAC
GAGCTGAGCC AGCGCCATGA GGAGCCCTGG AGGACGGGCA
AGCTGCTGCT GACACTGCCG CTGCTGCGGC AGACGGCCGC
CAAGGCCGTG CAGCACTTCT ATAGCGTCAA ACTGCAGGGC
AAAGTGCCCA TGCACAAACT CTTCCTGGAG ATGCTGGAGG
CCAAGGCCTG GGCCAGGGCT GACTCCCTTC AGGAGTGGAG
GCCACTGGAG CAAGTGCCCT CTCCCCTCCA CCGAGCCACC
AAGAGGCAGC ATGTGCATTT CCTAACTCCC TTGCCCCCTC
CCCCATCTGT GGCCTGGGTG GGCACTGCTC AGGCTGGATA
CCACCTGGAG GTTTTCCTTC CGCAGAGGGC AGGTTGGCCA
AGAGCAGCTT AGAGGATCTC CCAAGGATGA AAGAATGTCA
AGCCATGATG GAAAATGCCC CTTCCAATCA GCTGCCTTCA
CAAGCAGGGA TCAGAGCAAC TCCCCGGGGA TCCCCAATCC
ACGCCCTTCT AGTCCAACCC CCCTCAATGA GAGAGGCAGG
CAGATCTCAC CCAGCACTAG GACACCAGGA GGCCAGGGAA
AGCATCTCTG GCTCACCATG TAACATCTGG CTTGGAGCAA
GTGGGTGTTC TGCACACCAG GCAGCTGCAC CTCACTGGAT
CTAGTGTTGC TGCGAGTGAC CTCACTTCAG AGCCCCTCTA
GCAGAGTGGG GCGGAAGTCC TGATGGTTGG TGTCCATGAG
GTGGAAG.
```

10. A DNA molecule of claim 9 which comprises from nucleotide 950 to nucleotide 2452 of SEQ ID NO:1.

11. An expression vector for expressing a human nNR1 protein wherein said expression vector comprises the DNA molecule of claim 9.

12. An expression vector for expressing a human nNR1 protein wherein said expression vector comprises a DNA molecule of claim 11.

13. A host cell which expresses a recombinant human nNR1 protein wherein said host cell contains the expression vector of claim 11.

14. A host cell which expresses a recombinant human nNR1 protein wherein said host cell contains the expression vector of claim 12.

15. A process for expressing a human nNR1 protein in a recombinant host cell, comprising:
(a) transfecting the expression vector of claim 11 into a suitable host cell; and,
(b) culturing the host cells of step (a) under conditions which allow expression of said the human nNR1 protein from said expression vector.

16. A purified DNA molecule encoding a human nNR1 protein wherein said DNA molecule consists of the nucleotide sequence as set forth in SEQ ID NO:1, as follows:

```
                                          (SEQ ID NO:1)
GAATATGATG ACCCTAATGC AACAATATCT AACATACTAT

CCGAGCTTCG GTCATTTGGA AGAACTGCAG ATTTTCCTCC

TTCAAAATTA AAGTCAGGTT ATGGAGAACA TGTATGCTAT

GTTCTTGATT GCTTCGCTGA AGAAGCATTG AAATATATTG

GTTTCACCTG GAAAAGGCCA ATATACCCAG TAGAAGAATT

AGAAGAAGAA AGCGTTGCAG AAGATGATGC AGAATTAACA

TTAAATAAAG TGGATGAAGA ATTTGTGAA GAAGAGACAG

ATAATGAAGA AAACTTTATT GATCTCAACG TTTTAAAGGC

CCAGACATAT CACTTGGATA TGAACGAGAC TGCCAAACAA

GAAGATATTT TGGAATCCAC AACAGATGCT GCAGAATGGA

GCCTAGAAGT GGAACGTGTA CTACCGCAAC TGAAAGTCAC

GATTAGGACT GACAATAAGG ATTGGAGAAT CCATGTTGAC

CAAATGCACC AGCACAGAAG TGGAATTGAA TCTGCTCTAA

AGGAGACCAA GGGATTTTTG GACAAACTCC ATAATGAAAT

TACTAGGACT TTGAAAAGA TCAGCAGCCG AGAAAAGTAC

ATCAACAATC AGCCGGGAGC CCATGGAGCA CTGTCCTCAG

AGATGCGCAG GTTAGGCTCA CTGTCTAGGC CAGGCCCACC

TTAGTCACTG TGGACTGGCA ATGGAAGCTC TTCCTGGACA

CACCTGCCCT AGCCCTCACC CTGGGGTGGA AGAGAAATGA

GCTTGGCTTG CAACTCAGAC CATTCCACGG AGGCATCCTC

CCCTTCCCTG GGCTGGTGAA TAAAAGTTTC CTGAGGTCAA

GGACTTCCTT TTCCCTGCCA AAATGGTGTC CAGAACTTTG

AGGCCAGAGG TGATCCAGTG ATTTGGGAGC TGCAGGTCAC

ACAGGCTGCT CAGAGGGCTG CTGAACAGGA TGTCCTCGGA

CGACAGGCAC CTGGGCTCCA GCTGCGGCTC CTTCATCAAG

ACTGAGCCGT CCAGCCCGTC CTCGGGCATA GATGCCCTCA

GCCACCACAG CCCCAGTGGC TCGTCCGACG CCAGCGGCGG

CTTTGGCCTG GCCCTGGGCA CCCACGCCAA CGGTCTGGAC

TCGCCACCCA TGTTTGCAGG CGCCGGGCTG GGAGGCACCC

CATGCCGCAA GAGCTACGAG GACTGTGCCA GCGGCATCAT

GGAGGACTCG GCCATCAAGT GCGAGTACAT GCTCAACGCC

ATCCCCAAGC GCCTGTGCCT CGTGTGCGGG GACATTGCCT

CTGGCTACCA CTACGGCGTG GCCTCCTGCG AGGCTTGCAA

GGCCTTCTTC AAGAGGACTA TCCAAGGGAA CATTGAGTAC

AGCTGCCCGG CCACCAACGA GTGCGAGATC ACCAAACGGA

GGCGCAAGTC CTGCCAGGCC TGCCGCTTCA TGAAATGCCT

CAAAGTGGGG ATGCTGAAGG AAGGTGTGCG CCTTGATCGA

GTGCGTGGAG GCCGTCAGAA ATACAAGCGA CGGCTGGACT

CAGAGAGCAG CCCATACCTG AGCTTACAAA TTTCTCCACC

TGCTAAAAAG CCATTGACCA AGATTGTCTC ATACCTACTG

GTGGCTGAGC CGGACAAGCT CTATGCCATG CCTCCCCCTG

GTATGCCTGA GGGGACATC AAGGCCCTGA CCACTCTCTG

TGACCTGGCA GACCGAGAGC TTGTGGTCAT CATTGGCTGG

GCCAAGCACA TCCCAGGCTT CTCAAGCCTC TCCCTGGGGG

ACCAGATGAG CCTGCTGCAG AGTGCCTGGA TGGAAATCCT

CATCCTGGGC ATCGTGTACC GCTCGCTGCC CTACGACGAC

AAGCTGGTGT ACGCTGAGGA CTACATCATG GATGAGGAGC

ACTCCCGCCT CGCGGGGCTG CTGGAGCTCT ACCGGGCCAT

CCTGCAGCTG GTACGCAGGT ACAAGAAGCT CAAGGTGGAG

AAGGAGGAGT TTGTGACGCT CAAGGCCCTG GCCCTCGCCA

ACTCCGATTC CATGTACATC GAGGATCTAG AGGCTGTCCA

GAAGCTGCAG GACCTGCTGC ACGAGGCACT GCAGGACTAC

GAGCTGAGCC AGCGCCATGA GGAGCCTGG AGGACGGGCA

AGCTGCTGCT GACACTGCCG CTGCTGCGGC AGACGGCCGC

CAAGGCCGTG CAGCACTTCT ATAGCGTCAA ACTGCAGGGC

AAAGTGCCCA TGCACAAACT CTTCCTGGAG ATGCTGGAGG

CCAAGGCCTG GGCCAGGGCT GACTCCCTTC AGGAGTGGAG

GCCACTGGAG CAAGTGCCCT CTCCCCTCCA CCGAGCCACC

AAGAGGCAGC ATGTGCATTT CCTAACTCCC TTGCCCCCTC

CCCCATCTGT GGCCTGGGTG GGCACTGCTC AGGCTGGATA

CCACCTGGAG GTTTTCCTTC CGCAGAGGGC AGGTTGGCCA

AGAGCAGCTT AGAGGATCTC CCAAGGATGA AAGAATGTCA

AGCCATGATG GAAAATGCCC CTTCCAATCA GCTGCCTTCA

CAAGCAGGGA TCAGAGCAAC TCCCCGGGGA TCCCCAATCC

ACGCCCTTCT AGTCCAACCC CCCTCAATGA GAGAGGCAGG

CAGATCTCAC CCAGCACTAG GACACCAGGA GGCCAGGGAA

AGCATCTCTG GCTCACCATG TAACATCTGG CTTGGAGCAA

GTGGGTGTTC TGCACACCAG GCAGCTGCAC CTCACTGGAT

CTAGTGTTGC TGCGAGTGAC CTCACTTCAG AGCCCCTCTA

GCAGAGTGGG GCGGAAGTCC TGATGGTTGG TGTCCATGAG

GTGGAAG.
```

17. A DNA molecule of claim 16 which consists of nucleotide 950 to nucleotide 2452 of SEQ ID NO:1.

18. An expression vector for expressing a human nNR1 protein wherein said expression vector comprises the DNA molecule of claim 16.

19. An expression vector for expressing a human nNR1 protein wherein said expression vector comprises the DNA molecule of claim 17.

20. A host cell which expresses a recombinant human nNR1 protein wherein said host cell contains the expression vector of claim 18.

21. A host cell which expresses a recombinant human nNR1 protein wherein said host cell contains the expression vector of claim 19.

22. A process for expressing a human nNR1 protein in a recombinant host cell, comprising:

(a) transfecting the expression vector of claim 18 into a suitable host cell; and, (b) culturing the host cells of step (a) under conditions which allow expression of said the human nNR1 protein from said expression vector.

* * * * *